(12) United States Patent
Benkwitz et al.

(10) Patent No.: US 10,724,059 B2
(45) Date of Patent: Jul. 28, 2020

(54) FERMENTATION PROCESS

(71) Applicants: LanzaTech New Zealand Limited, Auckland (NZ); Frank Benkwitz, Auckland (NZ); Christophe Daniel Mihalcea, Auckland (NZ); Alice Marie Havill, Auckland (NZ)

(72) Inventors: Frank Benkwitz, Auckland (NZ); Christophe Daniel Mihalcea, Auckland (NZ); Alice Marie Havill, Auckland (NZ)

(73) Assignee: LANZATECH NEW ZEALAND LIMITED, Skokie, IL (US)

(*) Notice: Subject to any disclaimer, the term of this patent is extended or adjusted under 35 U.S.C. 154(b) by 693 days.

(21) Appl. No.: 14/360,645

(22) PCT Filed: Dec. 5, 2012

(86) PCT No.: PCT/NZ2012/000226
§ 371 (c)(1),
(2) Date: May 26, 2014

(87) PCT Pub. No.: WO2014/088427
PCT Pub. Date: Jun. 12, 2014

(65) Prior Publication Data
US 2015/0337343 A1    Nov. 26, 2015

(51) Int. Cl.
*C12P 7/54* (2006.01)
*C12P 7/18* (2006.01)
(Continued)

(52) U.S. Cl.
CPC .............. *C12P 7/54* (2013.01); *C12M 21/04* (2013.01); *C12M 29/24* (2013.01); *C12M 43/06* (2013.01);
(Continued)

(58) Field of Classification Search
None
See application file for complete search history.

(56) References Cited

U.S. PATENT DOCUMENTS

| 5,173,429 A | 12/1992 | Gaddy et al. |
| 5,593,886 A | 1/1997 | Gaddy |

(Continued)

FOREIGN PATENT DOCUMENTS

| NZ | 556615 | 8/2008 |
| WO | WO1998/00558 | 1/1998 |

(Continued)

OTHER PUBLICATIONS

Wikipedia, http://web.archive.org/web/20111103210835/http://en.wikipedia.org/wiki/Biomass, archived Nov. 3, 2011, accessed Jul. 21, 2016.*

(Continued)

*Primary Examiner* — Erin M. Bowers
(74) *Attorney, Agent, or Firm* — Frank S Molinaro

(57) ABSTRACT

This invention relates generally to method for producing products, particularly alcohols, by microbial fermentation. In particular, the invention relates to methods for increasing the efficiency of the fermentation, by providing a method for treating the used fermentation broth to produce a treated permeate which is then passed back to the bioreactor. The invention provides a method whereby at least one treatment step used to treat the permeated, produces a gaseous product which is then used in one or more stages of the fermentation process.

18 Claims, 14 Drawing Sheets

(51) Int. Cl.
| | |
|---|---|
| C12P 7/06 | (2006.01) |
| C12P 7/16 | (2006.01) |
| C12M 1/00 | (2006.01) |
| C12M 1/107 | (2006.01) |
| C12P 7/52 | (2006.01) |

(52) U.S. Cl.
CPC ............... *C12P 7/06* (2013.01); *C12P 7/065* (2013.01); *C12P 7/16* (2013.01); *C12P 7/18* (2013.01); *C12P 7/52* (2013.01); *Y02E 50/10* (2013.01); *Y02E 50/17* (2013.01); *Y02E 50/343* (2013.01)

(56) References Cited

U.S. PATENT DOCUMENTS

| | | | |
|---|---|---|---|
| 5,807,722 | A | 9/1998 | Gaddy |
| 5,821,111 | A | 10/1998 | Grady et al. |
| 6,136,577 | A | 10/2000 | Gaddy |
| 6,340,581 | B1 | 1/2002 | Gaddy |
| 6,368,819 | B1 | 4/2002 | Gaddy et al. |
| 6,753,170 | B2 | 6/2004 | Gaddy et al. |
| 7,078,201 | B2 | 7/2006 | Burmaster |
| 7,972,824 | B2 * | 7/2011 | Simpson .............. C12P 7/14 435/155 |
| 8,293,509 | B2 * | 10/2012 | Simpson .............. C12P 7/065 435/132 |
| 2009/0021513 | A1 | 8/2009 | Datta et al. |
| 2010/0120104 | A1 | 5/2010 | Reed |
| 2011/0026919 | A1 | 11/2011 | Kshirsagar |
| 2012/0008828 | A1 | 4/2012 | Gaddy |
| 2012/0088282 | A1 | 4/2012 | Gaddy |

FOREIGN PATENT DOCUMENTS

| | | | |
|---|---|---|---|
| WO | WO2000/68407 | | 11/2000 |
| WO | WO2002/08438 | | 1/2002 |
| WO | WO 2009/113878 | | 9/2007 |
| WO | WO2007/117157 | | 10/2007 |
| WO | WO 2007/117157 | * | 10/2007 |
| WO | WO2008/028055 | | 3/2008 |
| WO | WO2008/115080 | | 9/2008 |
| WO | WO2009/022925 | | 2/2009 |
| WO | WO2009/058028 | | 5/2009 |
| WO | WO2009/064200 | | 5/2009 |
| WO | WO 2009/064201 | | 5/2009 |
| WO | 2012-074543 A1 | | 6/2012 |

OTHER PUBLICATIONS

Wikipedia, http://web.archive.org/web/20111211005116/http://en.wikipedia.org/wiki/Biomaterial, archived Dec. 11, 2011, accessed Jul. 21, 2016.*
Klasson et al., Enz. Microb. Technol. 14: 602-608 (1992).*
Ashcroft et al., Nature 352: 225-226 (1991).*
Kopke, Michael et al., 2,3 butanediol production by acetogenic bacteria, an alternative route to chemical synthesis, using industrial waste gas, Appl. Environ. Microbiol., Jun. 17, 2011, vol. 77, No. 15, pp. 5567-5475.
Abrini, J., Naveau, H., & Hyns, E.J., Archives of Microbiology, (1994), 161, 345-351.
D.R. Martin, A. Misra and H. L. Drake, Dissimilation of Carbon Monoxide to Acetic Acid by Glucose-Limited Cultures of Clostridium thermoaceticum, Applied and Environmental Microbiology, (1985), vol. 49, No. 6, pp. 1412-1417.
Demler, M., Weuster-Botz, Reaction Engineering Analysis of Hydrogenotrophic Production of Acetic Acid by Acetobacterum Woodii, Biotechnology and Bioengineering, Feb. 2011, vol. 108, No. 2.
Hensirisak et. al. Scale-up of microbubble dispersion generator for aerobic fermentation, Applied Biochemistry and Biotechnology, Oct. 2002, vol. 101, No. 3.
J. L. Vega, et al., Study of Gaseous Substrate Fermentation: Carbon Monoxide Conversion to Acetate. 2. Continuous Culture, Biotech. Bioeng, (1989), 34. 6. 785-793.
J. L. Vega, et al., Study of gaseous substrate fermentations: Carbon monoxide conversion to acetate. 1. Batch culture, Biotechnology and Bioengineering, (1989), 34. 6. 774-784.
J. L. Vega, et al., Design of Bioreactors for Coal Synthesis Gas Fermentations. Resources, Conservation and Recycling, (1990), 3. 149-160.
K. T. Klasson, et al., Bioreactor design for synthesis gas fermentations, Fuel, (1991), 70. 605-614.
K. T. Klasson, et al., Bioreactors for synthesis gas fermentations resources, Conservation and Recycling, (1991), 5; 145-165.
K. T. Klasson et al., Bioconversion of synthesis gas into liquid or gaseous fuels, Enzyme and Microbial Technology, (1992), 14; 602-608.
Liou et al., International Journal of Systematic and Evolutionary Microbiology, (2005), 33: pp. 2085-2091.
M. Demler and D.Weuster-Botz, Reaction Engineering Analysis of Hydrogenotrophic Production of Acetic Acid by Acetobacterium woodii, Biotechnology and Bioengineering (2010).
Sakai et al., Biotechnology Letters, (2004), 29, pp. 1607-1612.
Simpa et. al., Critical Reviews in Biotechnology, 2006, vol. 26. pp. 41-65.
Svetlichny, V.A., Sokolova, T.G. et al., Systematic and Applied Microbiology (1991), 14: 254-260.
New Zealand First Examination Report for New Zealand Patent Application 708502, New Zealand Intellectual Property Office, dated Jul. 27, 2017.
Nagamani, B. et al., Biogas production technology: An Indian perspective, Current Science, Jul. 10, 1999, pp. 44-55, vol. 77, No. 1.
Zieminski, K. et al. Methane fermentation process as anaerobic digestion of biomass: Transformations, stages and microorganisms, African Journal of Biotechnology, Mar. 1, 2012, vol. 11(18), pp. 4127-4139.
Indian Examination Report for Indian Patent Application 4745/DELNP/2015, Indian Intellectual Property Office, dated Aug. 31, 2018.
European Examination Report for European Patent Application 12889517.4, dated Jan. 9, 2019, European Patent Office.
European Search Report for European Patent Application 12889517.4, European Patent Office, dated Jun. 16, 2016.

* cited by examiner

FERMENTATION PROCESS

CROSS REFERENCE TO RELATED APPLICATION

This application is a Continuation of copending PCT Application No. PCT/NZ/2012/000226 which was filed Dec. 5, 2012, which is incorporated herein by reference in its entirety.

FIELD OF THE INVENTION

This invention relates generally to method for producing products, particularly alcohols, by microbial fermentation. In particular, the invention relates to methods for increasing the efficiency of the fermentation, by providing a method for treating the used fermentation broth to produce a treated permeate which is then passed back to the bioreactor.

BACKGROUND OF THE INVENTION

Ethanol is rapidly becoming a major hydrogen-rich liquid transport fuel around the world. Worldwide consumption of ethanol in 2002 was an estimated 10.8 billion gallons. The global market for the fuel ethanol industry has also been predicted to grow sharply in future, due to an increased interest in ethanol in Europe, Japan, the USA and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, or as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major free energy-rich by-product of the incomplete combustion of organic materials such as coal or oil and oil derived products. For example, the steel industry in Australia is reported to produce and release into the atmosphere over 500,000 tonnes of CO annually.

It has long been recognised that catalytic processes may be used to convert gases consisting primarily of CO and/or CO and hydrogen ($H_2$) into a variety of fuels and chemicals. However, micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as their sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al, Archives of Microbiology 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to Green House Gas emissions.

The importance of controlling parameters of the liquid nutrient medium used for culturing bacteria or micro-organisms within a bioreactor used for fermentation has been recognised in the art. NZ 556615, filed 18 Jul. 2007 and incorporated herein by reference, describes, in particular, manipulation of the pH and the redox potential of such a liquid nutrient medium. For example, in the culture of anaerobic acetogenic bacteria, by elevating the pH of the culture to above about 5.7 while maintaining the redox potential of the culture at a low level (−400 mV or below), the bacteria convert acetate produced as a by-product of fermentation to ethanol at a much higher rate than under lower pH conditions. NZ 556615 further recognises that different pH levels and redox potentials may be used to optimise conditions depending on the primary role the bacteria are performing (i.e., growing, producing ethanol from acetate and a gaseous CO-containing substrate, or producing ethanol from a gaseous containing substrate).

U.S. Pat. No. 7,078,201 and WO 02/08438 also describe improving fermentation processes for producing ethanol by varying conditions (e.g. pH and redox potential) of the liquid nutrient medium in which the fermentation is performed.

The pH of the liquid nutrient medium may be adjusted by adding one or more pH adjusting agents or buffers to the medium. For example, bases such as NaOH and acids such as sulphuric acid may be used to increase or decrease the pH as required. The redox potential may be adjusted by adding one or more reducing agents (e.g. methyl viologen) or oxidising agents. Alternatively the pH of the medium may be adjusted by providing an excess amount of the gaseous substrate to the fermentation such that the microorganisms are "oversupplied" with gas.

Similar processes may be used to produce other alcohols, such as butanol, as would be apparent to one of skill in the art.

Regardless of the source used to feed the fermentation reaction, problems can occur when there are breaks in the supply. More particularly, such interruptions can be detrimental to the efficiency of the micro-organisms used in the reaction, and in some cases, can be harmful thereto. For example, where CO gas in an industrial waste gas stream is used in fermentation reactions to produce acids/alcohols, there may be times when the stream is not produced. During such times, the micro-organisms used in the reaction may go into hibernation. When the stream is available again, there may then be a lag before the micro-organisms are fully productive at performing the desired reaction.

Whereas ethanol can be easily removed from the stream of fermentation broth by applying heat, other metabolites such as acetic acid and 2,3-butanediol resulting from this process are more difficult to remove and may pose problems when the liquid returned into the process still contains these, even at low concentrations.

It is an object of the present invention to provide a system and/or a process that goes at least some way towards overcoming the above disadvantages, or at least to provide the public with a useful choice.

SUMMARY OF THE INVENTION

In a first aspect of the invention there is provided a method for microbial fermentation of a substrate comprising CO, the method comprising;
  a) in a bioreactor comprising a culture of one or more microorganisms, fermenting a gaseous substrate comprising CO to produce a fermentation broth comprising one or more products;
  b) passing at least a portion of the broth via a bleed stream, from the bioreactor;
  c) passing at least a portion of a permeate stream from the bioreactor;
  d) removing at least a portion of the one or more products from the bleed stream and/or permeate stream to provide a product depleted stream;
  e) passing the product depleted stream to a clarifying module wherein at least a portion of one or more components of the product depleted stream selected from the group consisting of biomass, proteins, organic components, or inorganic components is removed from the product depleted stream to provide a treated stream; and
  f) passing at least a portion of the treated stream to the bioreactor.

In one embodiment, the one or more products is an alcohol or an acid. In one embodiment the alcohol is selected from the group consisting of ethanol, butanol, propanol, propionate and 2,3-butanediol In one embodiment the acid is selected from the group consisting of acetic acid, butyric acid and propionic acid.

In one embodiment the one or more products are ethanol, 2,3-butanediol and acetate.

In one embodiment the one or more microorganisms of step (a) is a carboxydotrophic acetogenic bacteria. In one embodiment the one or more microorganisms is selected from the group consisting of *Clostridium autoethanogenum*, *Clostridium ljungdahlii*, *Clostridium ragsdalei*, *Clostridium carboxidivorans* and *Clostridium coskatii*.

In one embodiment the clarifying module comprises one or more of; a biomass removal module; an alcohol recovery module; a filter module; an acid removal module, an organic removal module; a sterilisation module or an inorganic removal module.

In one embodiment an alcohol recovery module is a distillation module.

In one embodiment, the biomass removal module is an anaerobic digestion module; an aerobic digestion module; or a filtration module.

In one embodiment the filter module is a nano-filtration module or a reverse osmosis module.

In one embodiment the organic removal module is an activated carbon module.

In one embodiment the inorganic removal module is an ion exchange module.

In one embodiment the acid removal module is an electrodialysis module or an activated carbon module.

In one embodiment the sterilisation module is an ultra violet sterilisation module, or a reverse osmosis module.

In a second aspect of the invention there is provided a method for microbial fermentation of a substrate comprising CO, the method comprising;
  a. in a bioreactor comprising a culture of one or more microorganisms, fermenting a gaseous substrate comprising CO to produce a fermentation broth comprising one or more products;
  b. passing at least a portion of the broth via a bleed stream, from the bioreactor;
  c. passing at least a portion of a permeate stream from the bioreactor;
  d. removing at least a portion of the one or more alcohols from the bleed stream and/or permeate stream to provide a product depleted stream;
  e. passing the product depleted stream to an anaerobic digestion stage, wherein at least a portion of one or more components selected from the group consisting of organic components and biomass are removed from the product deleted stream to provide a treated stream and a gaseous by-product;
  f. passing at least a portion of the treated stream to the bioreactor;
  g) using at least a portion of the gaseous by-product of step (e) as a heat, energy or carbon source for one or more steps of the microbial fermentation.

In one embodiment, the one or more products is an alcohol or an acid. In one embodiment the alcohol is selected from the group consisting of ethanol, butanol, propanol, propionate and 2,3-butanediol In one embodiment the acid is selected from the group consisting of acetic acid, butyric acid and propionic acid. In one embodiment the one or more products are ethanol and acetic acid. In one embodiment the one or more products are ethanol, 2,3-butanediol and acetic acid.

In one embodiment the one or more microorganisms of step (a) is a carboxydotrophic acetogenic bacteria. In one embodiment the one or more microorganisms is selected from the group consisting of *Clostridium autoethanogenum*, *Clostridium ljungdahlii*, *Clostridium ragsdalei*, *Clostridium carboxidivorans* and *Clostridium coskatii*.

In one embodiment the removed one or more products of step (d) are recovered.

In one embodiment of the invention the treated stream is passed through one or more optional clarifying steps prior to being passed to the bioreactor. The one or more optional clarifying steps include a biomass removal module; an alcohol recovery module, a filter module, or an acid removal module, an organic removal module, a sterilisation module, an inorganic removal module (i.e. ion exchange module). The one or more optional clarifying steps produce a clarified stream wherein at least a portion one or more components of the treated depleted stream is removed. The one or more components of the treated stream include but are not limited to products, organic components and inorganic components.

In one embodiment one or more nutrients, metals or salts are added to the clarified stream or the treated stream prior to the clarified stream or treated stream being passed to the bioreactor.

In one embodiment of the invention metals are added to the treated stream and/or clarified stream before the treated stream and/or clarified stream is passed to the bioreactor. In certain embodiments, one or more metals are selected from the group consisting of; Iron, Potassium, Calcium, Magnesium, Boron, Cobalt, Chromium, Manganese, Molybdenum, Sodium, Nickel, Selenium, Zinc, Chloride, Phosphorus, Sulphide, Nitrogen and Tungsten. In alternative embodiments the one or more metals are added to the fermentation broth after the treated stream and/or clarified stream has been passed back to the bioreactor.

In one embodiment of the invention one or more B vitamins are added to the treated stream and/or clarified stream before the treated stream and/or clarified stream is returned to the bioreactor. The one or more B vitamins are selected from the group comprising thiamine (B1), riboflavin (B2), niacin (B3), Pantothenic acid (B5), pyridoxine (B6), Folic acid (B9), Cyanocobalamin (B12), In one embodiment of the invention fresh media is blended with the treated stream and/or clarified stream In one embodiment at least a portion of one or more product components of the treated stream is removed during one or more clarifying steps, such that the one or more product components are prevented from accumulating in the bioreactor. In one embodiment the one or more product components is an alcohol or an acid.

In one embodiment the treated stream and/or clarified stream has an acid concentration of less than 10 g/L, or less than 8 g/L, or less than 6 g/L, or less than 4 g/L, or less than 2 g/L.

In one embodiment at least a portion of one or more inorganic components of the treated stream is removed during one or more clarifying steps, such that the one or more inorganic components are prevented from accumulating in the bioreactor.

In one embodiment at least a portion of one or more organic components of the treated stream is removed during one or more clarifying steps, such that the one or more organic components are prevented from accumulating in the bioreactor.

In one embodiment the gaseous by-product of step (e) is methane and/or carbon dioxide.

In one embodiment the methane produced by the anaerobic digestion is used as a heat, energy or carbon source for one or more steps of the microbial fermentation. In one embodiment the methane is reformed to produce carbon monoxide which is passed to the bioreactor for use as a substrate. In one embodiment the methane is passed to a gas turbine for power generation. In one embodiment the methane is passed to a steam boiler for direct or indirect heating of a distillation process.

Embodiments of the first aspect are analogous with the second aspect of the invention.

According to a third aspect of the present invention, there is provided a method for improving microbial fermentation of a substrate comprising CO, the method comprising;

a. fermenting a substrate comprising CO in a first bioreactor comprising a culture of one or more acetogenic microorganisms to produce a fermentation broth comprising one or more alcohols and optionally acetate;

b. passing at least a portion of the broth via a bleed stream from the first bioreactor to a second bioreactor;

c. passing at least a portion of a permeate stream from the first bioreactor to the second bioreactor;

d. fermenting a substrate comprising CO in the second bioreactor comprising a culture of one or more acetogenic microorganisms, to produce a fermentation broth comprising one or more alcohols and optionally acetate;

e. removing at least a portion of the broth via a bleed stream from the second bioreactor;

f. removing at least a portion of the permeate stream from the second bioreactor;

g. combining the bleed stream and the permeate stream to produce a combined stream;

h. treating the combined stream to remove at least a portion of the one or more products and provide a product depleted stream, i. treating the product depleted stream to remove at least a portion of the biomass and proteins;

j. passing the treated stream of step (i) to the primary bioreactor of step (a).

In particular embodiments of the invention, a portion of bleed stream and/or permeate exiting the first bioreactor is collected for product extraction, disposal or recycling.

In one embodiment, the treated permeate is treated to remove at least a portion of one or more acids, to reduce the acid concentration in the treated permeate. In one embodiment of the invention, the one or more acids comprise acetic and/or lactic acid. In particular embodiments substantially all of the acetic acid in the treated permeate is removed, such that a substantially acetate free permeate is passed to the first bioreactor.

In particular embodiments of the invention, a portion of the bleed stream exiting the first bioreactor is collected for product extraction, disposal or recycling.

In particular embodiments, microbial biomass is maintained in the second bioreactor by operating the second bioreactor in continuous or semi-continuous mode, wherein the second bioreactor is provided with cell retention means. In particular embodiments, the cell retention means is one or more cross-flow membranes. In another embodiment, the cell retention means is one or more hollow fibre membranes.

Embodiments of the first and second aspects are analogous with the third aspect of the invention.

In a fourth aspect of the invention there is provided a method for microbial fermentation of a substrate comprising CO2 and H2, the method comprising;

a. in a bioreactor comprising a culture of one or more microorganisms, fermenting a gaseous substrate comprising CO2 and H2 to produce a fermentation broth comprising one or more acids;

b. passing at least a portion of the broth via a bleed stream, from the bioreactor;

c. passing at least a portion of a permeate stream from the bioreactor;

d. removing at least a portion of the one or more acids from the bleed stream and/or permeate stream to provide an acid depleted stream;

e. passing the acetate depleted stream to a clarifying module wherein at least a portion of one or more components of the acid depleted stream selected from the group consisting of: biomass, proteins, organic components, or inorganic components is removed from the product depleted stream to provide a treated stream; and f. passing at least a portion of the treated stream to the bioreactor.

In one embodiment, the one or more acids is selected from the group consisting of acetic acid, butyric acid, propionic acid. In one embodiment the acid is acetic acid.

In one embodiment the one or more microorganisms is selected from the group consisting of *Moorella* species or *Acetobacterium* species. In one embodiment the one or more microorganism is *Acetobacterium woodii*.

In one embodiment the clarifying module comprises one or more of; a biomass removal module; an alcohol recovery module; a filter module; an acid removal module, an organic removal module; a sterilisation module or an inorganic removal module.

In one embodiment the clarifying module comprises one or more of; a biomass removal module; an alcohol recovery module; a filter module; an acid removal module, an organic removal module; a sterilisation module or an inorganic removal module.

In one embodiment an alcohol recovery module is a distillation module.

In one embodiment, the biomass removal module is an anaerobic digestion module; an aerobic digestion module; or a filtration module.

In one embodiment the filter module is a nano-filtration module or a reverse osmosis module.

In one embodiment the organic removal module is an activated carbon module

In one embodiment the inorganic removal module is an ion exchange module.

In one embodiment the acid removal module is an electro dialysis module or an activated carbon module.

In one embodiment, the bioreactor is a two reactor system.

Embodiments of the first, second and third aspects are analogous with the fourth aspect of the invention.

In one embodiment of any of the above aspects, the method further comprises recycling the bleed stream and permeate stream more than once. In certain embodiments, the bleed streams and permeates streams are treated and recycled through the system continuously. In certain embodiments additional medium is added to the system as required.

Although the invention is broadly as defined above, it is not limited thereto and also includes embodiments of which the following description provides examples.

BRIEF DESCRIPTION OF THE DRAWINGS

The invention will now be described in more detail and with reference to the accompanying figures, in which.

DETAILED DESCRIPTION OF THE INVENTION

Definitions

Figure 1:
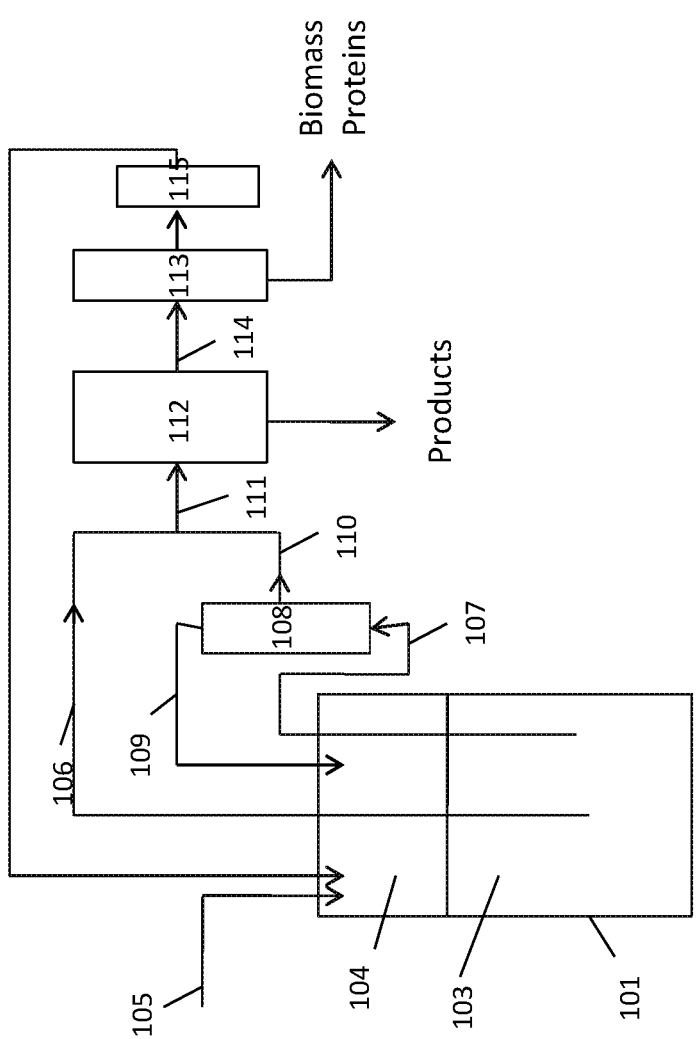
FIG. 1 is a schematic representation of a system and method according to one embodiment of the invention.

Unless otherwise defined, the following terms as used throughout this specification are defined as follows:

Dilution rate—the rate of replacement of the broth in a bioreactor. The dilution rate is measured in the number of bioreactor volumes of broth that are replaced by nutrient medium per day.

Fermentation broth or broth—the mixture of components (including the broth culture and nutrient medium) found in the bioreactor.

Nutrient medium—the solution added to the fermentation broth containing nutrients and other components appropriate for the growth of the microorganism culture.

Substrate comprising carbon monoxide—and like terms should be understood to include any substrate in which carbon monoxide is available to one or more strains of bacteria for growth and/or fermentation, for example.

Bleed stream—the portion of the fermentation broth removed from a bioreactor that is not passed to a separator.

Permeate stream—substantially soluble constituents of the broth that pass through the separator and are not retained by the separator. The permeate will typically contain soluble fermentation products, by-products and nutrient solution.

Product depleted stream—the portion of a bleed stream and/or a permeate stream that has been treated to remove at least a portion of one or more fermentation products.

Treated stream—the portion of a product depleted stream that has been treated to remove at least a portion of one or more components. The one or more components include but are not limited to biomass, protein and organic components.

Clarified Stream—the portion of a treated stream that has undergone one or more further treatment stages to remove at least a portion of one or more components, including but not limited to biomass, organic components, inorganic components and fermentation products.

Broth culture—the microorganism culture present in the fermentation broth.

Broth culture density—the density of microorganism cells in the fermentation broth.

Separator—a module that is adapted to receive fermentation broth from a bioreactor and pass the broth through a filter to yield a retentate and a permeate. The filter may be a membrane, e.g. cross-flow membrane or a hollow fibre membrane.

Gaseous substrate comprising carbon monoxide—and like terms includes any gas which contains carbon monoxide. The gaseous substrate will typically contain a significant proportion of CO, preferably at least about 5% to about 100% CO by volume.

Acid—as used herein this term includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

Bioreactor or fermenter—includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

Second or secondary bioreactor—as used herein these terms are intended to encompass any number of further bioreactors that may be connected in series or in parallel with the first and/or second bioreactors. Any one or more of these further bioreactors may also be connected to a further separator.

Fermenting, fermentation process or fermentation reaction—and like terms as used herein, are intended to encompass both the growth phase and product biosynthesis phase of the process. As is described further herein, in some embodiments the bioreactor may comprise a first growth reactor and a second fermentation reactor. As such, the addition of metals or compositions to a fermentation reaction should be understood to include addition to either or both of these reactors.

Product as used herein is intended to encompass substances produced by the microbial fermentation. Product can include alcohols, acids or other chemicals. Products can also include gases produced by the microbial fermentation process.

Organic components—molecules contained within the fermentation broth that predominantly consist of a Carbon back bone, with Hydrogen, Nitrogen and/or Oxygen surrounding the Carbon structure. Examples of organic compounds within the fermentation can include but are not restricted to Biomass, Ethanol, 2,3 Butanediol and Acetic Acid Inorganic components-non-carbon structured molecules contained within the broth that are not of biological origin. Examples of inorganic compounds within the fermentation broth can include, but are not limited to metals and salts including Magnesium, Potassium, Calcium and Iron compounds While the following description focuses on particular embodiments of the invention, namely the production of ethanol and/or acetate using CO as the primary substrate, it should be appreciated that the invention may be applicable to production of alternative alcohols and/or acids and the use of alternative substrates as will be known by persons of ordinary skill in the art to which the invention relates. For example, gaseous substrates containing carbon dioxide and hydrogen may be used. Further, the invention may be applicable to fermentation to produce acetic acid, butyric acid, propionic acid, butyrate, propionate, caproate, ethanol, propanol, butanediol and butanol. The methods may also be of use in producing hydrogen. By way of example, these products may be produced by fermentation using microbes from the genus *Moorella, Clostridia, Ruminococcus, Acetobacterium, Eubacterium, Butyribacterium, Oxobacter, Methanosarcina* and *Desulfotomaculum*.

In accordance with the invention, there is provided a method of producing products including alcohol(s) by fermentation of a CO containing substrate in a bioreactor. Products produced during fermentation are present in the fermentation broth and may be toxic to the broth culture or inhibit its production efficiency. In order to avoid these problems, a portion of the broth is typically regularly removed from the bioreactor to lower the by-product concentration but this also results in a portion of the broth culture being removed and disposed of. This depletion of the broth culture can affect the product yield.

The requirement to replenish the broth culture by growth (cell division) also means that the dilution rate is limited by the rate of growth of the broth culture; if the dilution rate is too high, the broth culture density drops too low and yields less product. Continual or batch removal of the broth requires that growth of the broth culture is prioritised so as to replenish the population. Since optimal growth conditions may differ to optimal product formation conditions, the removal of the broth can inhibit the ability of the culture to yield useful products. Furthermore continual removal of the broth and replenishment with fresh medium, requires a high usage of water and nutrients required in the medium.

In accordance with the invention, there is provided a method of treating used broth and permeate exiting the bioreactor, to enable the broth and permeate to be re-cycled through the bioreactor system.

The bleed stream and permeate exiting the fermentation system will contain products which may be toxic to the broth culture or inhibit its production efficiency. To overcome the problems associated with recycling the broth and permeate directly to a bioreactor, the bleed stream and permeate stream exiting the fermentation system undergo a number of treatment steps to remove products which may have an inhibitory effect on the fermentation. Further, the treated permeate may require the addition of nutrients, metals and/or vitamins that were lost during the fermentation process.

The treatment system of the present invention typically includes at least one treatment module selected from the group comprising; a biomass removal module; an alcohol recovery module, a filter module, or an acid removal module, an organic removal module, a sterilisation module, an inorganic removal module (i.e. ion exchange module).

Biomass Removal Module

Biomass may be removed from the bleed stream exiting the bioreactor by any known means. Typical methods for removing biomass from a fermentation broth include but are not limited to digestion methods, flocculation and sedimentation. In certain embodiments of the invention, removal of biomass is not required.

In certain aspects of the invention, the biomass removal module comprises an anaerobic digestion step. In one embodiment, the anaerobic digestion step consumes biomass and proteins and produces a gaseous substrate comprising CO2 and methane. In certain embodiments the methane produced by the anaerobic digestion is used on one or more steps of the method of the current invention. In one embodiment, the methane is reformed using know methods to provide a substrate comprising CO. The CO comprising substrate is then passed to the bioreactor where it is utilised as a substrate for the fermentation of one or more products. In another embodiment, the methane is passed to a steam boiler for direct or indirect heating of a distillation process. In one embodiment the methane is passed to a gas turbine for power generation.

Alcohol Removal Module

Alcohol (Ethanol) may be removed from the fermentation broth, bleed stream or permeate stream by a variety of processes. Technologies for the removal of alcohol based on differences on boiling point and volatility include but are not limited to packed distillation, vapour stripping and partial condensation separation. Alcohol may also be removed by pressure swing distillation and pervaporation. Pressure swing distillation and pervaporation operate in a pressure change environment that results in a separation based on differences in partial pressure. Other methods for removing alcohol include Simulated Moving Bed (SMB), perstraction and liquid-liquid extraction. These methods utilise a solid phase and/or organic solvent that exhibit properties of high molecular affinity for ethanol, to strip the ethanol component from the broth or bleed.

Filter Module

A filtration module may be provided to filter contaminants or unwanted products from the broth stream, or to capture any biomass or alcohol not capture by the biomass removal module or alcohol removal module. In certain embodiments of the invention the filter module may not be required. The Filtration module may comprise one or more filtration steps, such as a reverse osmosis step, or a nano-filtration step. The filtration module can be directed to the removal of one or more unwanted components of the stream to be returned to the bioreactor, including one or more organic components, one or more inorganic components, biomass components, and protein components.

Acid Removal Module

According to certain embodiments of the invention, at least a portion of the acetic acid in the fermentation broth exiting the bioreactor is removed prior to the fermentation broth being recycled back to the bioreactor as a treated permeate stream. Acetic acid may be removed from the fermentation broth by any known means. One such method for the removal of acetic acid is by aerobic digestion. Aerobic digestion is a process wherein distilled permeate and waste are combined in a reactor and inoculated with a mixture of yeast and/or bacteria, capable of metabolising acetic acid, ethanol and 2,3-butanediol or other organic components to biomass and CO2. This process also produces heat as a by-product. Yeast and bacteria are removed from the broth by methods such as centrifugation or filtration. The resulting "treated permeate" is then returned to the primary bioreactor.

Alternative methods include anaerobic digestion wherein methane is produced in significant quantities in addition to the CO2 and biomass produced.

Organic Removal Module

It can be desired to reduce the organic content of the fermentation broth prior to recycling it to the bioreactors. Such organic content can include Ethanol, 2,3 Butanediol, Butanol, Isopropanol, 2,3 Butanedione, Acetoin. One such method is anaerobic digestion. Another is aerobic digestion. Another is Nanofiltration. Another is Reverse Osmosis. Removal is required to prevent inhibition to the fermentation and/or any detrimental effect on gas-liquid mass transfer.

In accordance with the invention, there is provided a method of producing products including alcohol(s) by fermentation of a CO containing substrate in a bioreactor.

According to an embodiment of the present invention represented in figure FIG. 1, there is provided a fermentation system comprising a bioreactor. In accordance with the methods of the invention, liquid nutrient media can be continuously or semi-continuously provided to bioreactor 101 via inlet 105. The separator 108 is adapted to receive at least a portion of broth 103 from the bioreactor via a first output conduit 107 and pass it through the separator 108 configured to substantially separate the microorganism cells (the retentate) from the rest of the fermentation broth (the permeate). At least a portion of the retentate is returned to the first bioreactor via a first return conduit 109 which ensures that the broth culture density is maintained at an optimal level. The separator 108 is adapted to pass at least a portion of the permeate stream out of the separator 108 via a permeate delivery conduit 110. Substantially cell free permeate is removed via permeate removal conduit 110 for product extraction, to be recycled or to be disposed of A bleed stream output 106 is provided to directly remove broth from the bioreactor for product extraction, to be recycled or to be disposed of.

In one embodiment the bioreactor 101 is configured to promote the production of microorganism products as well as the growth of a continuous inoculum. In this embodiment bleed stream is passed out of the bioreactor through a bleed output 106. The bleed stream and the permeate stream exiting the bioreactor are combined and the combined stream is passed to a product recovery means 112 via a conduit 111. At least a portion of one or more fermentation products is removed from the permeate and/or bleed stream. In certain embodiments the product recovery means is a distillation means. A product depleted stream is passed to a treatment module 114 via a conduit 113, for removal of one or more components of the product depleted stream. The treatment module 114 can include one or more of an anaerobic digestion means, an aerobic digestion means or a filtration means. In certain embodiments, at least a portion of biomass and/or proteins are removed by the treatment module. A treated stream exiting the treatment module 114 is passed to the bioreactor 101.

In certain embodiments the product depleted stream undergoes a further treatment step for the removal of one or more acids from the product depleted stream prior to the product depleted stream being passed to the treatment module. In certain embodiment the treated stream passed to the bioreactor contains substantially no acid.

In certain embodiments of the present invention, the treated stream is passed through an optional clarifying module 115 to provide a clarified stream. The clarifying module can include one or more of the following modules; an organic removal module, an inorganic removal module, an alcohol recovery module, a biomass removal module, a filter module, an acid removal module, or a sterilisation module.

Figure 2:
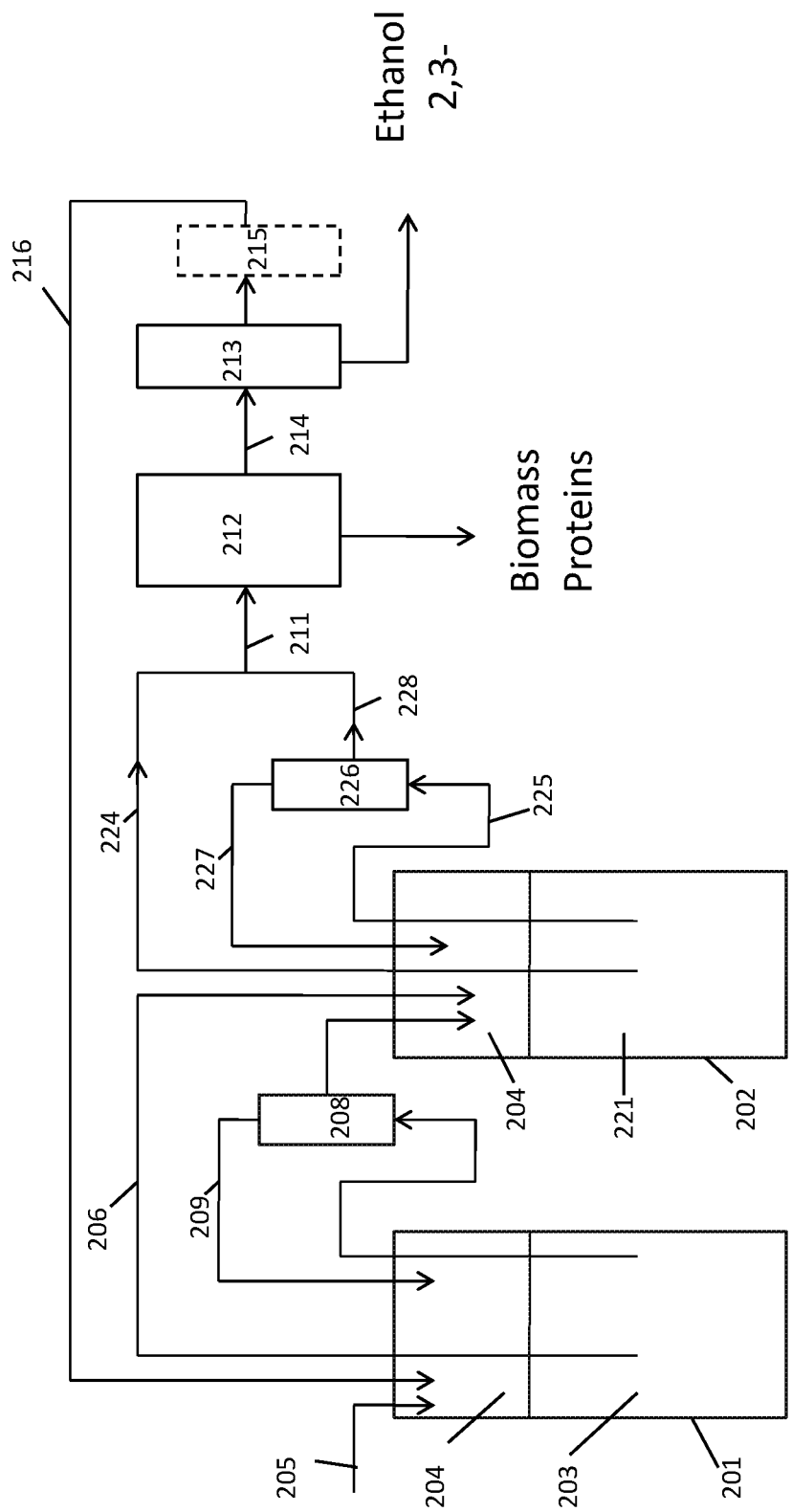
FIG. 2 is a schematic representation of a system and method according to a particular embodiment of the invention.

In certain embodiments, additional nutrient, metals and B-vitamins are added to the treated stream prior to the treated permeate being passed to the bioreactor 101. In other embodiments, additional nutrients, metals and B-vitamins are added to the bioreactor after the treated stream has been passed to the bioreactor. According to an embodiment of the present invention represented in FIG. 2, there is provided a fermentation system comprising a bioreactor. In accordance with the methods of the invention, liquid nutrient media can be continuously or semi-continuously provided to bioreactor 201 via inlet 205. The separator 208 is adapted to receive at least a portion of broth 203 from the bioreactor via a first output conduit 207 and pass it through the separator 208 configured to substantially separate the microorganism cells (the retentate) from the rest of the fermentation broth (the permeate). At least a portion of the retentate is returned to the first bioreactor via a first return conduit 209 which ensures that the broth culture density is maintained at an optimal level. The separator 208 is adapted to pass at least a portion of the permeate stream out of the separator 208 via a permeate delivery conduit 210. Substantially cell free permeate is removed via permeate removal conduit 210 for product extraction, to be recycled or to be disposed of A bleed stream output 206 is provided to directly remove broth from the bioreactor for product extraction, to be recycled or to be disposed of.

In one embodiment the bioreactor 201 is configured to promote the production of microorganism products as well as the growth of a continuous inoculum. In this embodiment bleed stream is passed out of the bioreactor through a bleed output 206. The bleed stream and the permeate stream exiting the bioreactor are combined and the combined stream is passed to a product recovery means 212 via a conduit 211. At least a portion of one or more fermentation products is removed from the permeate and/or bleed stream. In certain embodiments the product recovery means is a distillation means. A product depleted stream is passed to an anaerobic digestion module 214. In certain embodiments, at least a portion of biomass and/or proteins are removed by the anaerobic digestion module. In certain embodiments a gaseous stream comprising methane and carbon dioxide is produced as a by-product of the anaerobic digestion process. In certain embodiment the gaseous stream is captured and used as a carbon, energy or heat source. The methane in the gaseous stream can be reformed to provide a carbon monoxide substrate which is passed back to the bioreactor. Alternatively the methane is passed to a gas turbine for power generation. Alternatively the methane is passed to a steal boiler for direct or indirect heating of a distillation process.

A treated stream exiting the treatment module 214 is passed through a clarifying module 216 to provide a clarified stream. The clarifying module 215 can include one or more of the following modules; an organic removal module, an inorganic removal module, an alcohol recovery module, a biomass removal module, a filter module, an acid removal module, or a sterilisation module. The clarified stream is passed to the bioreactor 201.

In certain embodiments, additional nutrient, metals and B-vitamins are added to the treated stream prior to the clarified stream being passed to the bioreactor 201. In other embodiments, additional nutrients, metals and B-vitamins are added to the bioreactor after the clarified stream has been passed to the bioreactor.

Figure 3:
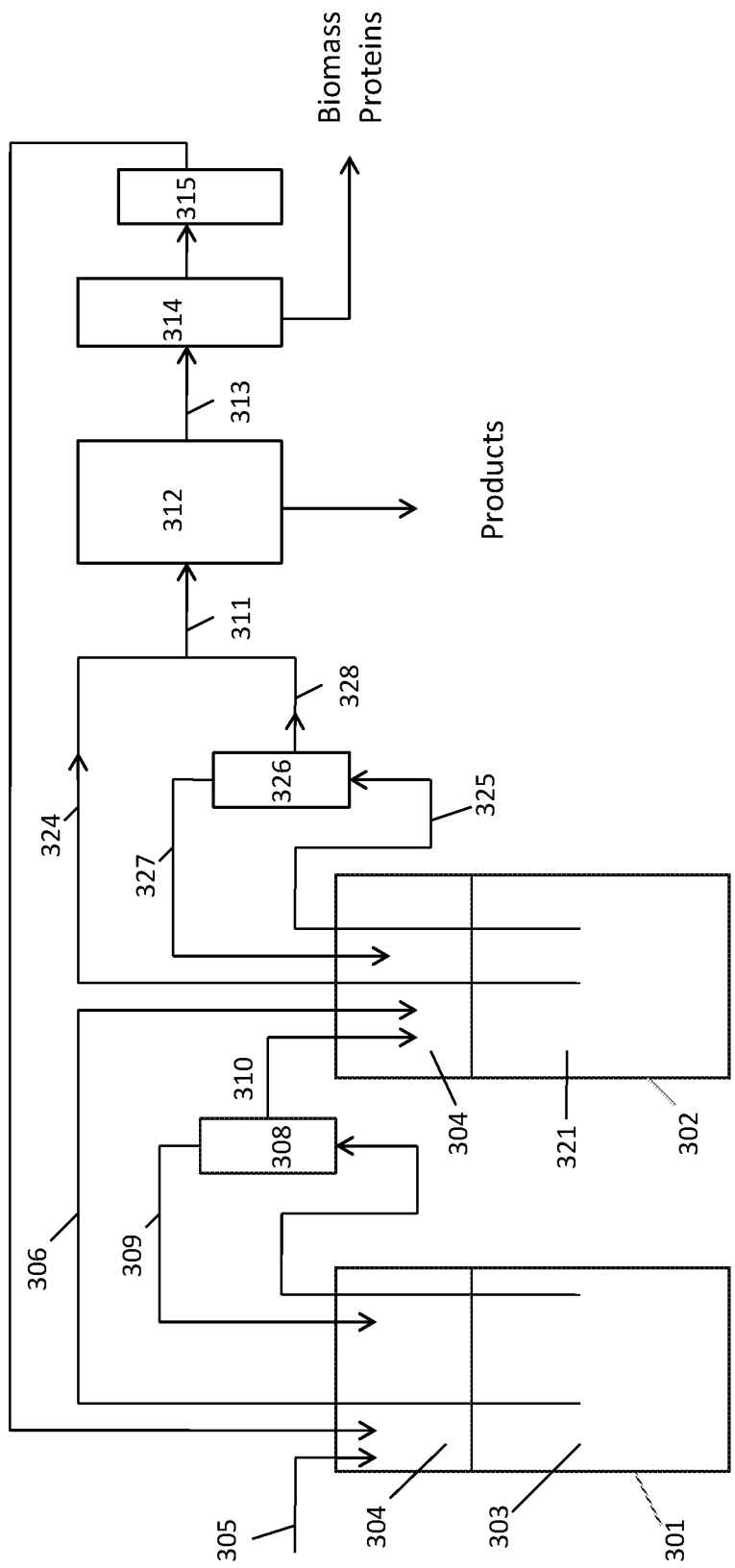
FIG. 3 is a schematic representation of a two fermenter system according to a particular embodiment of the present invention.

FIG. 3 shows a two reactor system according to one embodiment of the invention. Referring to FIG. 3, there is provided a fermentation system comprising a first bioreactor 301 linked to a second bioreactor 302 via a first separator 308. In accordance with the methods of the invention, liquid nutrient media can be continuously or semi-continuously provided to bioreactor 301 via inlet 305. The first separator 308 is adapted to receive at least a portion of broth 303 from the first bioreactor via a first output conduit 307 and pass it through the separator 308 configured to separate a portion of the microorganism cells (the retentate) from the rest of the fermentation broth (the permeate). At least a portion of the retentate is returned to the first bioreactor via a first return conduit 309 which ensures that the broth culture density is maintained at an optimal level. The separator 308 is adapted to pass at least a portion of the permeate to the second bioreactor 302 via a permeate delivery conduit 310 for addition to the second fermentation broth 321.

In this embodiment the first bioreactor 301 is configured to promote the production of microorganism products as well as the growth of a continuous inoculum to be passed directly into the secondary bioreactor 302 through a bleed stream output 306. During fermentation, the broth culture density is maintained by recycling at least a portion of the microorganism cells as retentate via the conduits 325 and 327 and a second separator 326. Substantially cell free permeate is removed via permeate removal conduit 328 for product extraction, to be recycled or to be disposed of A second bleed stream output 324 is provided to directly remove a bleed stream from the second bioreactor for product extraction, to be recycled or to be disposed of.

In accordance with one embodiment of the invention, the permeate and the second bleed stream exiting the second bioreactor 302 are combined to provide a combined stream. The combined stream is then processed in accordance with the description provided in FIGS. 1 and 2. In accordance with the invention, one or more secondary bioreactors are provided wherein at least a portion of permeate including alcohols and optionally acids pass from the first bioreactor via the separator into the second bioreactor. By passing the permeate containing the fermentation products and less desirable by-products to the second bioreactor, and retaining the retentate in the first bioreactor, the broth culture density can be maintained and broth culture growth can be prioritised if required.

In accordance with particular embodiments of the invention, a second (or further) separator is adapted to receive at least a portion of the broth and separate the microorganism cells (the retentate) from the rest of the fermentation broth (the permeate). The separator is adapted to pass at least a portion of the retentate back to the broth in order to replenish and maintain the broth culture. In particular embodiments, at least a portion of the permeate is removed from the system to be passed to a further system or to enable the products to be extracted according to known methods.

In particular embodiments, a portion of the broth from the first bioreactor is passed directly to the second bioreactor. This portion is referred to herein as the first bleed stream 6. Modulation of the ratio of bleed stream to permeate being passed to the second bioreactor may be used to control the culture density in the first and/or second bioreactors. In a further embodiment, a portion of the broth from the second bioreactor may be removed from the system to be passed to a further system or to enable the products to be extracted according to known methods. The ratio of bleed stream to permeate being removed from the second bioreactor may be used to control the culture density in the second bioreactor. Modulation of the culture density enables optimisation of the bioreactors for microorganism growth, product yield, or other desirable modes of operation.

In particular embodiments the permeate and bleed streams exiting at least one of the secondary bioreactors is collected. The combined stream is then treated to remove biomass and proteins and other contaminants. The combined stream is then passed to a distillation chamber for the recovery of one or more alcohol(s) and optionally acid(s). The alcohol depleted stream is filtered and/or digested and the treated permeate exiting is then passed into the primary bioreactor. In certain embodiments the treated permeate may be divided into one or more streams and may be passed into one or more of the primary bioreactor and secondary bioreactors.

In particular embodiments the treated permeate stream is provided with additional nutrients, metals and or vitamins prior to the treated permeate being passed to the one or more bioreactors. In certain embodiments the nutrients, metals and or vitamins are added to the bioreactor after the treated permeate has been passed to said bioreactor.

In particular embodiments the treated permeate being passed to the one or more bioreactors contains acetate at a concentration of less than 5 g/L acetate, or less than 4 g/L acetate, or less than 3 g/L, or less than 2 g/l acetate, or less than 1 g/L acetate, or substantially no acetate.

In known systems, if a higher rate of CO-containing substrate throughput is used in a bioreactor, higher relative alcohol production may be achieved but growth of the broth culture and production of acetate is reduced which negatively impacts the culture's health. This can lead to collapse of the microorganism cell population in the broth culture due to lack of growth. The inventors have shown that increasing broth culture density allows a higher throughput rate of CO-containing substrate to be used and results in an increased product yield.

In accordance with the invention, the method includes fermentation of a substrate comprising CO in a fermentation broth in a first bioreactor for optimal microbial growth, then passing at least a portion of the fermentation broth via a separator to a second bioreactor configured for optimal alcohol production. In particular embodiments, the rate of alcohol production in the secondary bioreactor is substantially greater than or equal to the rate in the first bioreactor.

In a particular embodiment, the first bioreactor is configured to function as a continuous inoculum bioreactor wherein fermentation conditions substantially promote microbial growth and optionally alcohol production. It is considered that optimum conditions for microbial growth occur at low alcohol conditions of less than 30 g/L; or less than 25 g/L; or less than 20 g/L; or less than 15 g/L; or less than 10 g/L of fermentation broth. In order to maintain such levels of alcohol, the fermentation is typically operated continuously, wherein nutrient media containing one or more essential nutrients necessary for microbial growth, such as nitrogen, phosphorus, potassium, sulfur, B-vitamins and trace metals, is continuously or semi-continuously fed to the first bioreactor. In accordance with the invention, a portion of the broth is removed to a separator and the retentate or a portion thereof is recycled to the first bioreactor. Alternatively, or in addition, broth may be removed from the bioreactor as bleed stream and passed to a second bioreactor. Removal of the broth via either or both routes allows an optimal growth rate to be maintained. In further embodiments, the dilution rate of the nutrient media entering the first bioreactor can be adjusted to promote optimal microbial growth.

In particular embodiments of the invention, the operating conditions of the secondary bioreactor are configured for alcohol production. Thus, in one or more secondary bioreactors, the alcohol production rate is at least approximately 70 g/L/d, at least approximately 100 g/L/d; at least approximately 150 g/L/d; at least approximately 180 g/L/d; at least approximately 200 g/L/d; at least approximately 230 g/L/d of the fermentation broth. However, in particular embodiments, the overall alcohol production rate across both bioreactors (or all bioreactors) is substantially the same as the production rate in the first bioreactor.

It is recognised that as alcohol accumulates in the secondary bioreactor(s), the specific rate of alcohol production (volumetric rate of alcohol production per unit mass of microbial cells) decreases as metabolism of the microbial cells decreases. The microbial culture will continue to grow in the secondary bioreactor, albeit at a slower rate. In accordance with the invention, a portion of the broth from the second bioreactor is passed to a separator which provides a retentate comprising microbial cells. The retentate is recycled to the secondary bioreactor and thus increases or maintains the broth culture density so that it is at a level sufficient to achieve a volumetric rate of alcohol production substantially equal to or greater than the volumetric rate of alcohol production in the first bioreactor.

In particular embodiments, during steady state fermentation, fermentation broth will be continuously provided from the first bioreactor via the separator or the bleed stream and broth with increased alcohol concentration will be continuously removed from the secondary bioreactor(s), such that a substantially constant volume is maintained in the secondary bioreactor(s).

The size and quantity of the first bioreactor and secondary bioreactor(s) can be selected to optimise each fermentation. However, in one embodiment, there is provided one first bioreactor and multiple smaller secondary bioreactors. In another embodiment, there is provided multiple first bioreactors and multiple similarly sized secondary bioreactors.

In particular embodiments the secondary bioreactor(s) is configured to operate in continuous, semi-continuous, fed batch or batch modes.

In a further embodiment, the method comprises recycling at least a portion of the first or second permeates and first or second bleed streams to the first or second bioreactor.

In a particular embodiment of any of the above aspects, the method further comprises the treatment of at least a portion of the first or second permeate and first and second bleed stream prior to or during recycling from the first or second separator to the first or second bioreactor. For example treatment may consist of removing contaminants including toxic and/or inhibitory products from the permeate and broth streams. Components removed from the permeate and bleed streams can include biomass, proteins, one or more alcohols, and one or more acids, one or more inorganic components. Treatment may further comprise replenishment of additional components or nutrients (such as B vitamins) being added to the permeate and/or the bleed stream to replenish the nutrient medium before it is returned to the bioreactor. Also, the pH of the permeate and/or bleed stream may be adjusted before being returned to the bioreactor to change or maintain the pH of the broth in the bioreactor.

Carbon Monoxide Fermentation

Certain embodiments of the invention are adapted to use gas streams produced by one or more industrial processes. Such processes include steel making processes, particularly processes which produce a gas stream having a high CO content or a CO content above a predetermined level (i.e., 5%). According to such embodiments, acetogenic bacteria are preferably used to produce acids and/or alcohols, particularly ethanol or butanol, within one or more bioreactors. Those skilled in the art will be aware upon consideration of the instant disclosure that the invention may be applied to various industries or waste gas streams, including those of vehicles with an internal combustion engine. Also, those skilled in the art will be aware upon consideration of the instant disclosure that the invention may be applied to other fermentation reactions including those using the same or different micro-organisms. It is therefore intended that the scope of the invention is not limited to the particular embodiments and/or applications described but is instead to be understood in a broader sense; for example, the source of the gas stream is not limiting, other than that at least a component thereof is usable to feed a fermentation reaction. The invention has particular applicability to improving the overall carbon capture and/or production of ethanol and other alcohols from gaseous substrates comprising CO. Processes for the production of ethanol and other alcohols from gaseous substrates are known. Exemplary processes include those described for example in WO2007/117157, WO2008/115080, WO2009/022925, WO2009/064200, U.S. Pat. Nos. 6,340,581, 6,136,577, 5,593,886, 5,807,722 and 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* has the identifying characteristics of DSMZ deposit number DSMZ 10061 or DSMZ23693. The laboratory strain of this bacterium is known as LZ1561.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactors, such as one or more continuous stirred tank reactor (CSTR), immobilised cell reactor(s), a gas-lift reactor(s), bubble column reactor(s) (BCR), membrane reactor (s), such as a Hollow Fibre Membrane Bioreactor (HFMBR) or trickle bed reactor(s) (TBR). Also, in some embodiments of the invention, the bioreactor(s) may comprise a first, growth reactor in which the micro-organisms are cultured, and a second, fermentation reactor, to which fermentation broth from the growth reactor is fed and in which most of the fermentation product (e.g. ethanol and acetate) is produced. In particular embodiments, the second bioreactor is different to the first bioreactor.

According to various embodiments of the invention, the carbon source for the fermentation reaction is a gaseous substrate containing CO. The substrate may be a CO-containing waste gas obtained as a by-product of an industrial process, or from another source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing substrate may be captured from the industrial process before it is emitted into the atmosphere, using any convenient method. Depending on the composition of the CO-containing substrate, it may also be desirable to treat it to remove any undesired impurities, such as dust particles before introducing it to the fermentation. For example, the gaseous substrate may be filtered or scrubbed using known methods.

Alternatively, the CO-containing substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 20% to about 100% CO by volume, from 43% to 95% CO by volume, from 60% to 90% CO by volume, and from 70% to 90% CO by volume. In particular embodiments, the substrate comprises 25%, or 30%, or 35%, or 40%, or 45%, or 50% CO by volume. Substrates having lower concentrations of CO, such as 6%, may also be appropriate, particularly when $H_2$ and $CO_2$ are also present.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In other embodiments, the substrate stream comprises concentrations of $H_2$ from 2% to 13%. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In particular embodiments, the substrate stream comprises CO2 and no or minimal CO.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemistry and Biotechnology* Volume 101, Number 3/October, 2002) could be used for this purpose.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/117157, WO2008/115080, WO2009/022925, WO2009/058028, WO2009/064200, WO2009/064201 and WO2009/113878, referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (for example microbial growth and/or ethanol production). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO07/117157, WO08/115080 and WO2009/022925.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that acetate production increases and ethanol production decreases.

Product Recovery

The products of the fermentation reaction can be recovered using known methods. Exemplary methods include those described in WO07/117157, WO08/115080, U.S. Pat. Nos. 6,340,581, 6,136,577, 5,593,886, 5,807,722 and 5,821,111. However, briefly and by way of example only, ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non-volatile and is recovered for re-use in the fermentation.

Acetate, which is produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed may also be returned to a fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Fermentation Utilising a Carbon Dioxide and Hydrogen Substrate.

The invention has particular applicability to supporting the production of acetate and ethanol from gaseous substrates such as $CO_2$ and $H_2$ containing industrial flue gases. One such type of gas stream is tailgas from hydrogen production plants, which typically contains 50-60% $CO_2$, 20-30% $H_2$, 5-15% CO, and 5-15% $CH_4$. Another industrial process resulting in a $CO_2$ and $H_2$ rich tail gas is ammonia manufacture. Similar streams are produced from processing of any carbon based feedstock, such as petroleum, coal, and biomass. The invention is also applicable to reactions which produce alternative alcohols.

Processes for the production of ethanol and other alcohols from gaseous substrates are known. Exemplary processes include those described for example in WO2007/117157, WO2008/115080, U.S. Pat. Nos. 6,340,581, 6,136,577, 5,593,886, 5,807,722 and 5,821,111, each of which is incorporated herein by reference.

A number of anaerobic bacteria are known to be capable of carrying out the fermentation of $CO_2$ and $H_2$ to alcohols, including ethanol, and acetic acid, and are suitable for use in the process of the present invention. Acetogens have the ability to convert gaseous substrates such as $H_2$, $CO_2$ and CO into products including acetic acid, ethanol and other fermentation products by the Wood-Ljungdahl pathway. Examples of such bacteria that are suitable for use in the invention include those of the genus *Acetobacterium*, such as strains of *Acetobacterium woodii* ((Demler, M., Weuster-Botz, "Reaction Engineering Analysis of Hydrogenotrophic Production of Acetic Acid by *Acetobacterum Woodii*", Biotechnology and Bioengineering, Vol. 108, No. 2, February 2011).

*Acetobacterium woodii* has been shown to produce acetate by fermentation of gaseous substrates comprising $CO_2$ and $H_2$. Buschhorn et al. demonstrated the ability of *A. woodii* to produce ethanol in a glucose fermentation with a phosphate limitation.

Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Morella thermoacetica*, *Moorella thermoautotrophica*, *Ruminococcus productus*, *Acetobacterium woodii*, *Eubacterium limosum*, *Butyribacterium methylotrophicum*, *Oxobacter pfennigii*, *Methanosarcina barkeri*, *Methanosarcina acetivorans*, *Desulfotomaculum kuznetsovii* (Simpa et. al. Critical Reviews in Biotechnology, 2006 Vol. 26. Pp41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Acetobacterium woodii* having the identifying characteristics of the strain deposited at the German Resource Centre for Biological Material (DSMZ) under the identifying deposit number DSM 1030.

Culturing of the bacteria used in a method of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: M. Demler and D. Weuster-Botz (2010). Reaction Engineering Analysis of Hydrogenotrophic Production of Acetic Acid by *Acetobacterium woodii*. Biotechnology and Bioengineering 2010; D. R. Martin, A. Misra and H. L. Drake (1985). Dissimilation of Carbon Monoxide to Acetic Acid by Glucose-Limited Cultures of *Clostridium thermoaceticum*. Applied and Environmental Microbiology, Vol 49, No. 6, pages 1412-1417. Typically, fermentation is carried out in any suitable bioreactor, such as a continuous stirred tank reactor (CTSR), a bubble column reactor (BCR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor is fed and in which most of the fermentation product (ethanol and acetate) is produced.

The $CO_2$ and $H_2$ Containing Substrate

Preferably the carbon source for the fermentation can be a gaseous substrate comprising carbon dioxide in combination with hydrogen. Similarly, the gaseous substrate may be a $CO_2$ and $H_2$ containing waste gas obtained as a by-product of an industrial process, or from some other source. The largest source of $CO_2$ emissions globally is from the combustion of fossil fuels such as coal, oil and gas in power plants, industrial facilities and other sources.

The gaseous substrate may be a $CO_2$ and $H_2$-containing waste gas obtained as a by-product of an industrial process, or from some another source such as from automobile exhaust fumes. In certain embodiments, the industrial process is selected from the group consisting of hydrogen manufacture, ammonia manufacture, combustion of fuels, gasification of coal, and the production of limestone and cement. The gaseous substrate may be the result of blending one or more gaseous substrates to provide a blended stream. It would be understood to a skilled person that waste gas streams rich in $H_2$ or rich in $CO_2$ are more abundant that waste gas streams rich in both $H_2$ and $CO_2$. A skilled person would understand that blending one or more gas streams comprising one of the desired components of $CO_2$ and $H_2$ would fall within the scope of the present invention.

Hydrogen rich gas streams are produced by a variety of processes including steam reformation of hydrocarbons, and in particular steam reformation of natural gas. The partial oxidation of coal or hydrocarbons is also a source of hydrogen rich gas. Other sources of hydrogen rich gas include the electrolysis of water, by-products from electrolytic cells used to produce chlorine and from various refinery and chemical streams.

Gas streams typically rich in Carbon dioxide include exhaust gasses from combustion of a hydrocarbon, such as natural gas or oil. Carbon dioxide is also produced as a by-product from the production of ammonia, lime or phosphate and from natural carbon dioxide wells.

Blending of Streams

As noted previously, it may be desirable to blend an industrial waste stream with one or more further streams in order to improve efficiency, acid and/or alcohol production and/or overall carbon capture of the fermentation reaction.

Accordingly, where industrial streams have a high $CO_2$ content, but include minimal or no $H_2$, it may be desirable to blend one or more streams comprising $H_2$ with the waste stream comprising $CO_2$, prior to providing the blended substrate stream to the fermenter. The overall efficiency, alcohol productivity and/or overall carbon capture of the fermentation will be dependent on the stoichiometry of the $CO_2$ and $H_2$ in the blended stream. However, in particular embodiments the blended stream may substantially comprise $CO_2$ and $H_2$ in the following molar ratios: at least 1:2 at least 1:4 or at least 1:6 or at least 1:8 or at least 1:10.

Blending of streams may also have further advantages, particularly in instances where a waste stream comprising $CO_2$ and or $H_2$ is intermittent in nature. For example, an intermittent waste stream comprising $CO_2$ and or $H_2$ may be blended with a substantially continuous stream comprising $CO_2$ and or $H_2$ and provided to the fermenter. In particular embodiments of the invention, the composition and flow rate of the substantially continuous stream may be varied in accordance with the intermittent stream in order to maintain provision of a substrate stream of substantially continuous composition and flow rate to the fermenter.

Blending of two or more streams to achieve a desirable composition may involve varying flow rates of all streams, or one or more of the streams may be maintained constant while other stream(s) are varied in order to 'trim' or optimise the substrate stream to the desired composition. For streams that are processed continuously, little or no further treatment (such as buffering) may be necessary and the stream can be provided to the fermenter directly. However, it may be necessary to provide buffer storage for streams where one or more is available intermittently, and/or where streams are available continuously, but are used and/or produced at variable rates.

Those skilled in the art will appreciate it will be necessary to monitor the composition and flow rates of the streams prior to blending. Control of the composition of the blended stream can be achieved by varying the proportions of the constituent streams to achieve a target or desirable composition. For example, a base load gas stream may be predominantly $CO_2$, and a secondary gas stream comprising a high concentration of $H_2$ may be blended to achieve a specified $H_2:CO_2$ ratio. The composition and flow rate of the blended stream can be monitored by any means known in the art. The flow rate of the blended stream can be controlled independently of the blending operation; however the rates at which the individual constituent streams can be drawn must be controlled within limits. For example, a stream produced intermittently, drawn continuously from buffer storage, must be drawn at a rate such that buffer storage capacity is neither depleted nor filled to capacity.

At the point of blending, the individual constituent gases will enter a mixing chamber, which will typically be a small vessel, or a section of pipe. In such cases, the vessel or pipe may be provided with static mixing devices, such as baffles, arranged to promote turbulence and rapid homogenisation of the individual components.

Buffer storage of the blended stream can also be provided if necessary, in order to maintain provision of a substantially continuous substrate stream to the bioreactor.

A processor adapted to monitor the composition and flow rates of the constituent streams and control the blending of the streams in appropriate proportions, to achieve the required or desirable blend may optionally be incorporated into the system. For example, particular components may be provided in an as required or an as available manner in order to optimise the efficiency of alcohol productivity and/or overall carbon capture.

In certain embodiments of the invention, the system is adapted to continuously monitor the flow rates and compositions of at least two streams and combine them to produce a single blended substrate stream of optimal composition, and means for passing the optimised substrate stream to the fermenter.

By way of non limiting example, particular embodiments of the invention involve the utilisation of carbon dioxide gas from lime or cement production as a source of $CO_2$. Typically, such streams contain little or no $H_2$, therefore it may be desirable to combine the stream comprising $CO_2$ with a stream comprising $H_2$ in order to achieve a more desirable $CO_2:H_2$ ratio. $H_2$ is often produced in large quantities at a steel mill in the coke oven. Accordingly, a waste stream from the coke oven comprising $H_2$ can be blended with a lime kiln waste stream comprising $CO_2$ to achieve a desirable composition.

Other sources of $CO_2$ and/or $H_2$ that may be blended to form a $CO_2/H_2$ substrate stream include ammonia and urea synthesis.

The gaseous substrate may also be a $CO_2$ and $H_2$-containing waste gas obtained from some other source such as from automobile exhaust fumes. In these embodiments, the $CO_2$ and $H_2$ containing gas may be captured from the industrial process before it is emitted into the atmosphere, using any convenient method. Depending on the composition of the gaseous $CO_2$ and $H_2$ containing substrate, it may also be desirable to treat it to remove any undesired impurities, such as dust particles before introducing it to the fermentation. For example, the gaseous substrate may be filtered or scrubbed using known methods.

The $CO_2$ and $H_2$ containing substrate may also be sourced from fermentation processes wherein carbohydrates or gases are fermented to form products such as ethanol. For example, the anaerobic fermentation of a gaseous substrate comprising CO by microorganisms from the genus *Clostridium* results in the production of products including ethanol. $CO_2$ and optionally hydrogen are by-products of the fermentation reaction.

In some embodiments of the invention, the substrate comprising $CO_2$ is derived from carbon containing waste, for example, industrial waste gases or from the gasification of other wastes. As such, the methods of the invention represent effective processes for capturing carbon that would otherwise be exhausted into the environment. In certain embodiments, the methods provide improved processes for capturing $CO_2$ by conversion into useful products such as acids and/or alcohols.

The $CO_2$ and $H_2$ containing substrate will typically contain a major proportion of $H_2$, such as at least about 30% $H_2$ by volume, or at least 40% $H_2$ by volume, or at least 50% $H_2$ by volume, or at least 60% $H_2$ by volume, or at least 70% $H_2$ by volume, or at least 80% $H_2$ by volume, or at least 85% $H_2$ by volume.

The gaseous substrate will typically contain at least about 10% $CO_2$ by volume, or at least 15% $CO_2$ by volume, or at least 20% $CO_2$ by volume, or at least 25% $CO_2$ by volume, or at least 30% $CO_2$ by volume, or at least 40% $CO_2$ by volume.

Methods for Separating $CO_2$ from other gaseous components are well known. Separation technologies can be sorted into three general categories; post-combustion, pre-combustion and oxyfuel. Post combustion technologies use solvents to absorb $CO_2$ from the flue gas after combustion. Pre-combustion technologies separate $CO_2$ from the feed fuel, using well known processes such as hydrocarbon gasification and water-shift reaction, and uses the remaining hydrogen gas as fuel. Oxyfuel plants replace air with pure oxygen in the combustion chamber. When burned with pure oxygen, hydro carbons emit an almost pure stream of $CO_2$ and steam, facilitating end separation of $CO_2$.

It would be understood by a skilled person that, a hydrocarbon stream can be passed through a number of processes in order to produce the substrate comprising $CO_2$ and $H_2$. For example, in accordance with one aspect of the invention a hydrocarbon stream ($CH_4$) passes through a Steam Methane Reformer to produce a gas stream comprising at least CO and $H_2$; the gas stream then undergoes a Water Gas Shift reaction to produce a substrate comprising CO, $CO_2$ and $H_2$. The substrate can be passed through a Pressure Swing Adsorber (PSA) to separate at least a portion of gases. IT would be understood that more than one PSA stage can be used to enable separation of different components of the gas stream.

As the skilled addressee would understand, the $CO_2$ component of the substrate and the $H_2$ component of the gas steam can be derived from separate sources. The $CO_2$ component can be derived from an industrial waste gas stream typically rich in carbon dioxide, and hydrogen from an alternative source can be blended with the $CO_2$ to produce a $CO_2$ and $H_2$ substrate having the desired composition. Known separation techniques can be used to separate out the desired components of each industrial waste gas, and the desired components can be blended together to form the substrate comprising $CO_2$ and $H_2$.

Typically the carbon dioxide will be added to the fermentation reaction in a gaseous state. However, the methods of the invention are not limited to the addition of carbon dioxide in this state. Carbon dioxide is readily dissolvable in water. At room temperature, the solubility of $CO_2$ is about 90 $cm^3$ of $CO_2$ per 100 ml of water. Carbon dioxide exists in many forms in aqueous solution. When added to an aqueous solution $CO_2$ dissolves.

$$CO_2(g) \rightarrow CO_2(aq)$$

Equilibrium between the dissolved $CO_2$ and hydrogen carbonate is then established;

$$CO_2 + H_2O(l) \leftrightharpoons H^+ + HCO_3$$

Hydrogen carbonate then dissociates;

$$HCO_3^- \leftrightharpoons H^+ + CO_3^{2-}$$

The amount of the various forms of carbon dioxide present in aqueous solution is dependent on the factors including pH of the solution, as well as pressure and temperature conditions. The presence of other ions in solution can also affect the amount of the different forms of carbon dioxide present in solution.

A skilled person would understand that Carbon dioxide could be provided to the fermentation in aqueous form. A skilled person would also understand that it would be possible to provide $CO_2$ to the fermentation reaction in both gaseous and aqueous forms.

Reaction Stoichiometry

Anaerobic bacteria have been demonstrated to produce ethanol and acetic acid from CO, $CO_2$ and $H_2$ via the Acetyl-CoA biochemical pathway.

The stoichiometry for the formation of acetate from a substrate comprising $H_2$ and $CO_2$ by acetogenic bacterial including *Acetobacterium woodii* is as follows (Balch et al., 1977):

$$4H_2 + 2CO_2 \rightarrow CH_3COOH + 2H_2O.$$

For growth of the bacteria and $CO_2$ and $H_2$-to-acid and/or alcohol fermentation to occur, in addition to the $CO_2$ and $H_2$-containing substrate gas, a suitable liquid nutrient medium will need to be fed to the bioreactor. A nutrient medium will contain vitamins and minerals sufficient to permit growth of the micro-organism used. Anaerobic media suitable for the fermentation of acetate and/or ethanol using $CO_2$ as the sole carbon source are known in the art. For example, suitable media are described in U.S. Pat. Nos. 5,807,722 and 6,340,581. The present invention provides a novel media which has increased efficacy in supporting growth of the micro-organisms and/or alcohol production in the fermentation process. This media will be described in more detail hereinafter.

The fermentation should desirably be carried out under appropriate conditions for the $CO_2$ and $H_2$-to-acetate and/or ethanol fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that $CO_2$ in the liquid phase does not become limiting, and maximum product concentrations to avoid product inhibition. Suitable conditions are described in WO02/08438, WO07/117157 and WO08/115080.

The optimum reaction conditions will depend partly on the particular micro-organism used. However, in general, it is preferred that the fermentation be performed at pressure higher than ambient pressure. Operating at increased pressures allows a significant increase in the rate of $CO_2$ transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

It is also desirable that the rate of introduction of the $CO_2$ and $H_2$ containing gaseous substrate is such as to ensure that the concentration of $CO_2$ and $H_2$ in the liquid phase does not become limiting. This is because a consequence of $CO_2$ and $H_2$-limited conditions may be that the ethanol product is consumed by the culture.

The optimum temperature for fastest growth of the bacteria, and highest production rate of acetate was determined by running the fermenter at a range of different temperature points. The fermenter was initially run at 30° C., and the temperature was increased to a number of different temperatures. It was surprisingly found that the optimum temperature for fastest growth of bacteria was at least 32° C., or at least 33° C., or at least 34° C., or at least 35° C., or at least 36° C.

EXAMPLES

Method and Materials for Waste Recycling Patent

Media:

| Solution A | | | |
|---|---|---|---|
| $NH_4Ac$ | 3.083 g | KCl | 0.15 g |
| $MgCl_2 \cdot 6H_2O$ | 0.61 g | | |
| $CaCl_2 \cdot 2H_2O$ | 0.294 g | Distilled Water | Up to 1 L |
| Solution(s) B | | | |
| Component | mol/L H2O | Component | mol/L H2O |
| $FeCl_3$ | 0.1 | $Na_2MoO_4$ | 0.01 |
| $CoCl_2$ | 0.05 | $ZnCl_2$ | 0.01 |
| $MCl_2$ | 0.05 | MnCl2 | 0.01 |
| $H_3BO_3$ | 0.01 | NTA | 0.3 |
| $Na_2SeO_3$ | 0.01 | | |
| Solution C | | | |
| Biotin | 20.0 mg | Calcium D-(*)-pantothenate | 50.0 mg |
| Folic acid | 20.0 mg | | |
| Pyridoxine•HCl | 10.0 mg | Vitamin B12 | 50.0 mg |
| Thiamine•HCl | 50.0 mg | p-Aminobenzoic acid | 50.0 mg |
| Riboflavin | 50.0 mg | Thioctic acid | 50.0 mg |
| Nicotinic acid | 50.0 mg | Distilled water | To 1 Liter |

Bacteria: *Clostridium autoethanogenum* (LZ1561) from Lanzatech stock.

Fermentation in Bioreactor:

Two-litre reactors were filled with 1.5 L of media containing all metals, phosphoric acid, B-Vitamins solutions specified in the tables above) and 3 g/L Ammonium acetate. The media was then degassed using 'real mill gas' (approximately 50% CO, 20% $CO_2$, 28% $N_2$ and 2% $H_2$). 0.5 M $Na_2S$ or 0.12 M $(NH_4)_2SO_3$ (pH 6.0) were added at a rate of 0.2 mL/h to deliver sulphur into the media before inoculation. The ORP ($AgCl_2$) was further adjusted to −200 mV with 0.2M $Cr^{2+}$ before inoculation with 200 mL culture from a continuously running seed fermenter with a biomass of approximately 2 g/L. pH, ORP, gas uptake and $H_2S$ in the headspace were closely monitored over the next hours to ensure a successful start up. The pH was controlled via managing the optimal delivery of gas to the culture and additionally backed up by automatic pH control (at 5.0) via 5M $NH_4OH$. For the first 24 hours the culture is a batch ferment and then switched to continuous mode by delivering at a rate to achieve a dilution rate between 2 and 3 and at the same time delivering $Na_2S$ or $(NH_4)_2SO_3$, the remaining metals and antifoam at the appropriate rates.

The continuous fermentation systems may include cell recycling or not. Hollow fibre membrane cartridges with a pore size of 0.1 μm are used for cell recycling. When reactors are joined to a 2- or 3-fermenter system the permeate resulting from cell recycling and the waste are transferred directly into the downstream fermenter. Thus the ratio between permeate and waste remains an estimate based on the dialed-in flow rates.

Sampling and Analytical Procedures:

Samples of the cultures were taken 4 times a day to measure the optical density (absorbance at 600 nm) using a spectrophotometer. From the same sample an aliquot was dedicated for HPLC (Agilent) analysis to quantify ethanol, acetic acid, 2,3-butanediol, lactic acid and phosphoric acid. The gas composition of the incoming and outgoing gas streams were analysed in hourly intervals on a micro GC (Varian) to quantify the different gases and monitor gas (CO) consumption.

Example 1

Recycling of Permeate in 2-Reactor System

Permeate is obtained by circulating fermentation broth continuously through a hollow fibre membrane removing the filtrate at a rate of approximately 50% of the media inflow rate. Permeate from reactor 2 of a two fermenter system with cell recycling in both fermenters, where both, waste and permeate, from reactor 1 are fed into reactor 2, was collected. The permeate was distilled and filtered through a filter. During the distillation process the ethanol and dissolved proteins were removed, whereas acetic acid and 2,3-butanediol remain in the permeate. LS03 B-Vitamin solution was added (20 mL/L salts and metals were added as is done for the preparation of fresh media. This distilled permeate was then fed back into the reactor 1 of the 2 fermenter system. Initially no obvious changes were observed in the reactor performance. After feeding of the distilled permeated began, a lowering in the production rate of acetic acid was observed. The experiment lasted for 240 hours. The viability of the bacteria in both fermenters was not affected at any stage of the experiment. On day 9 the gas uptake started to decline in both fermenters. As usual, hydrogen uptake was first/most obviously affected. On day 10 "second round permeate" was fed to the bioreactor. Second round permeate is permeate collected while the reactor was running on the distilled permeate described above.

Figure 4:
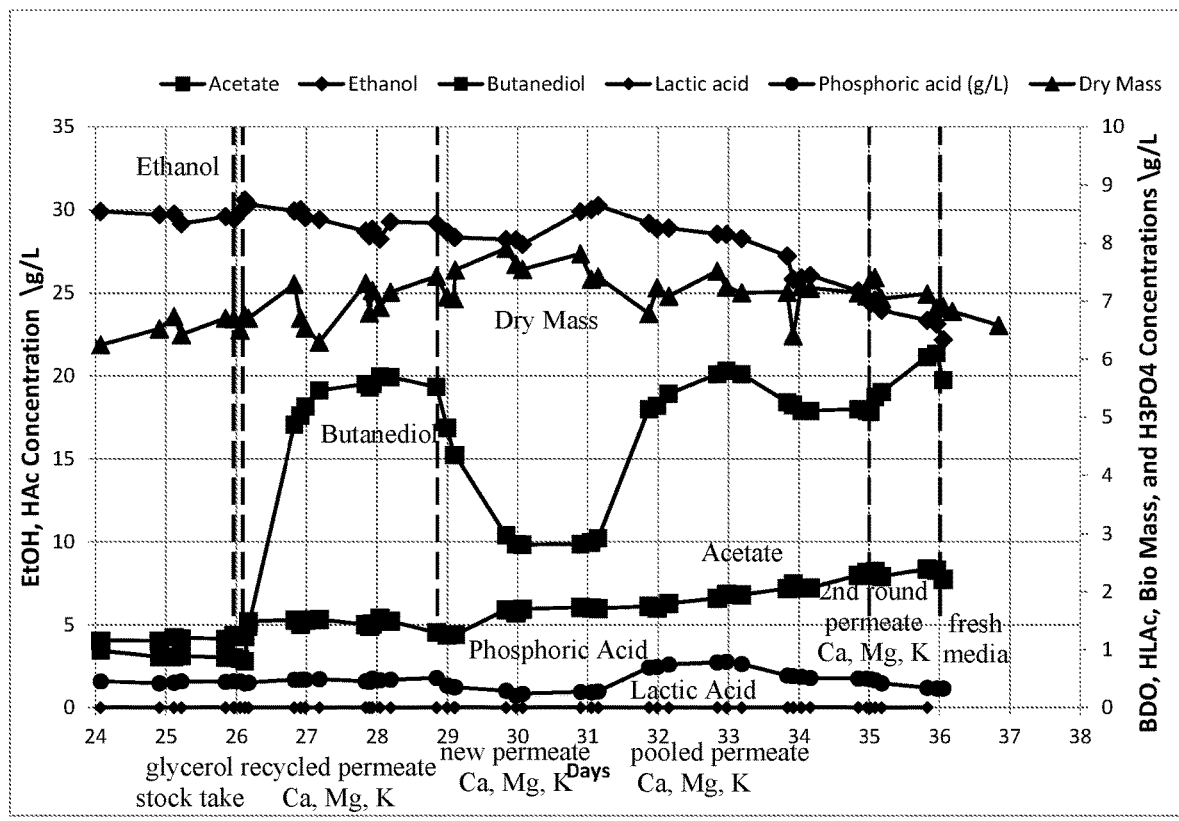
FIG. 4 is a graph showing the metabolite concentration in a first fermenter of a two fermenter system during permeate recycling.
Figure 5:
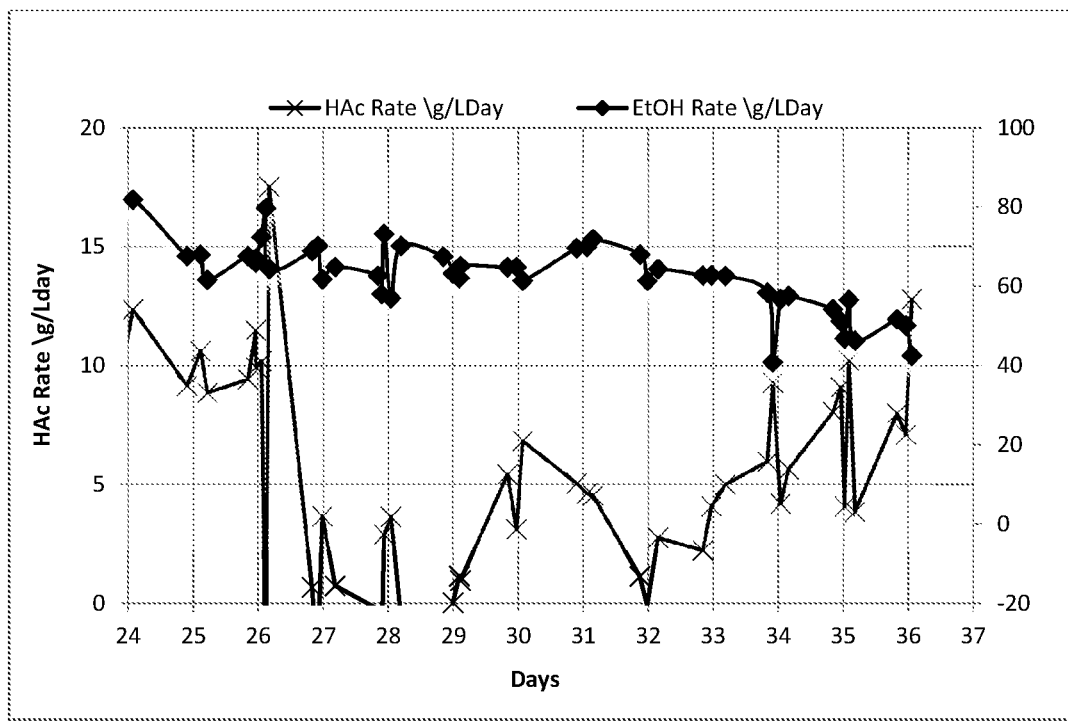
FIG. 5 is a graph showing acetic acid and ethanol production in the first fermenter referred to in FIG. 3.
Figure 6:
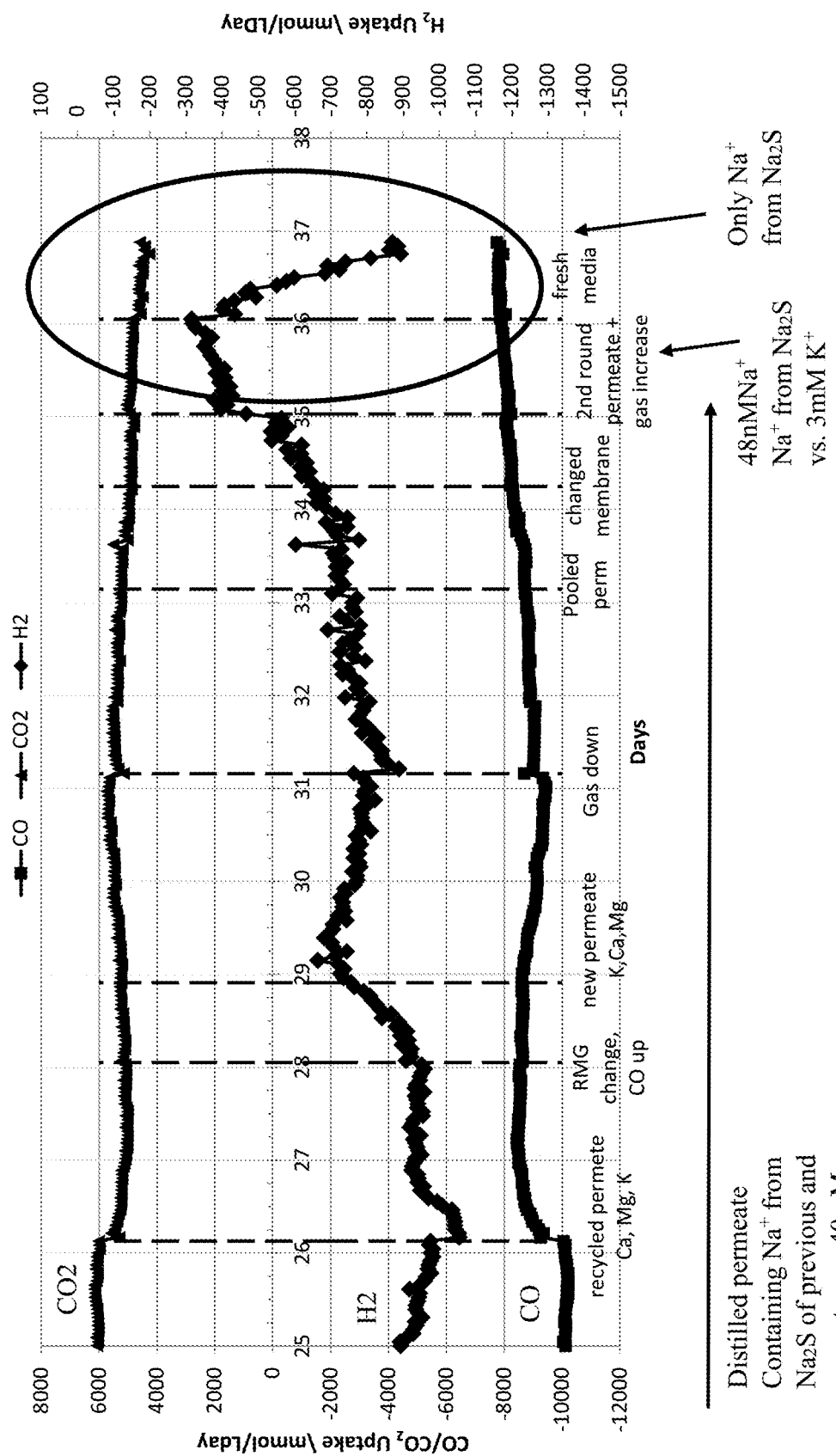
FIG. 6 is a graph showing gas uptake levels in the first fermenter referred to in FIG. 3.
Figure 7:
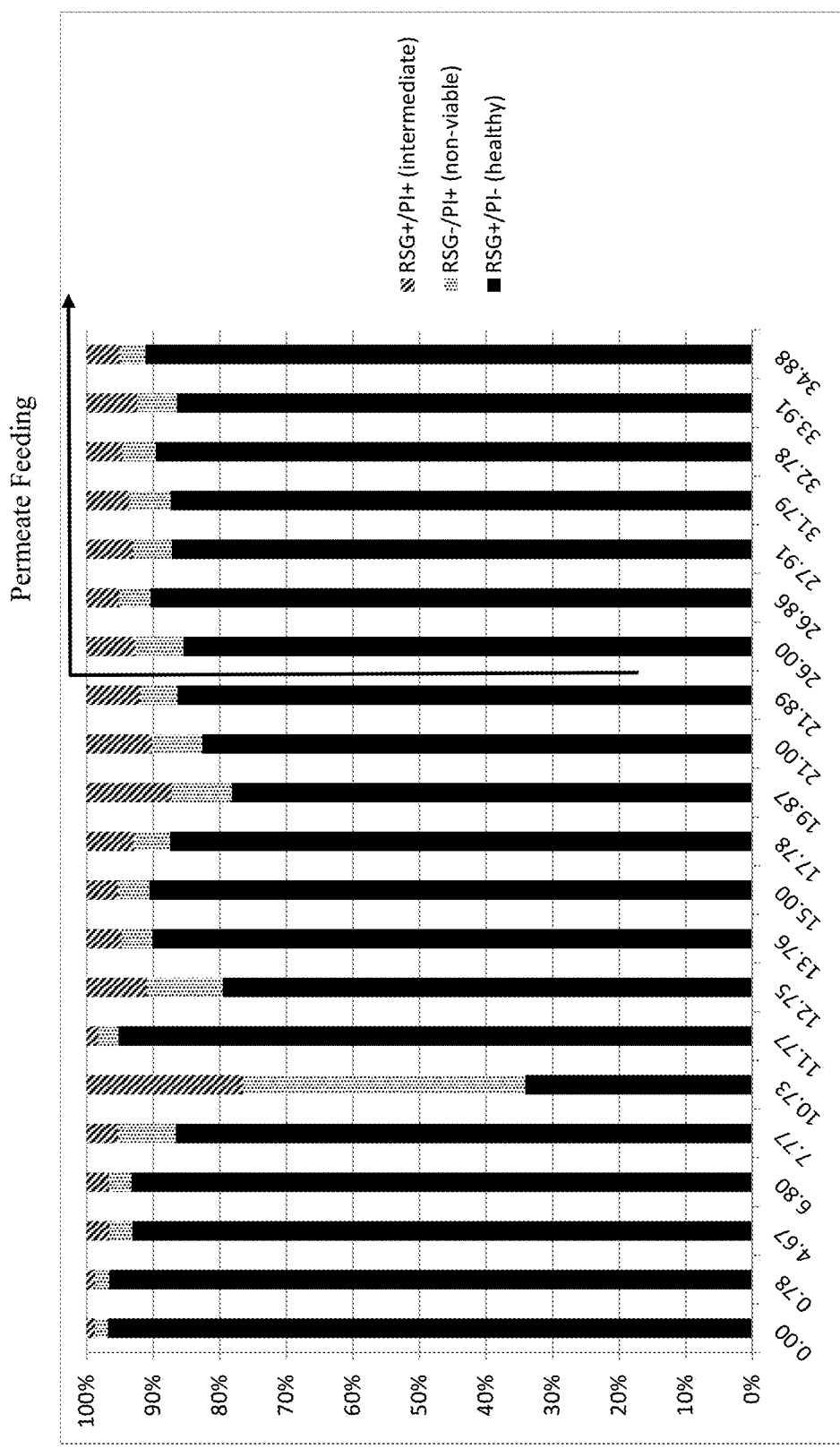
FIG. 7 a graph showing the cell viability in the first fermenter referred to in FIG. 3.
Figure 8:
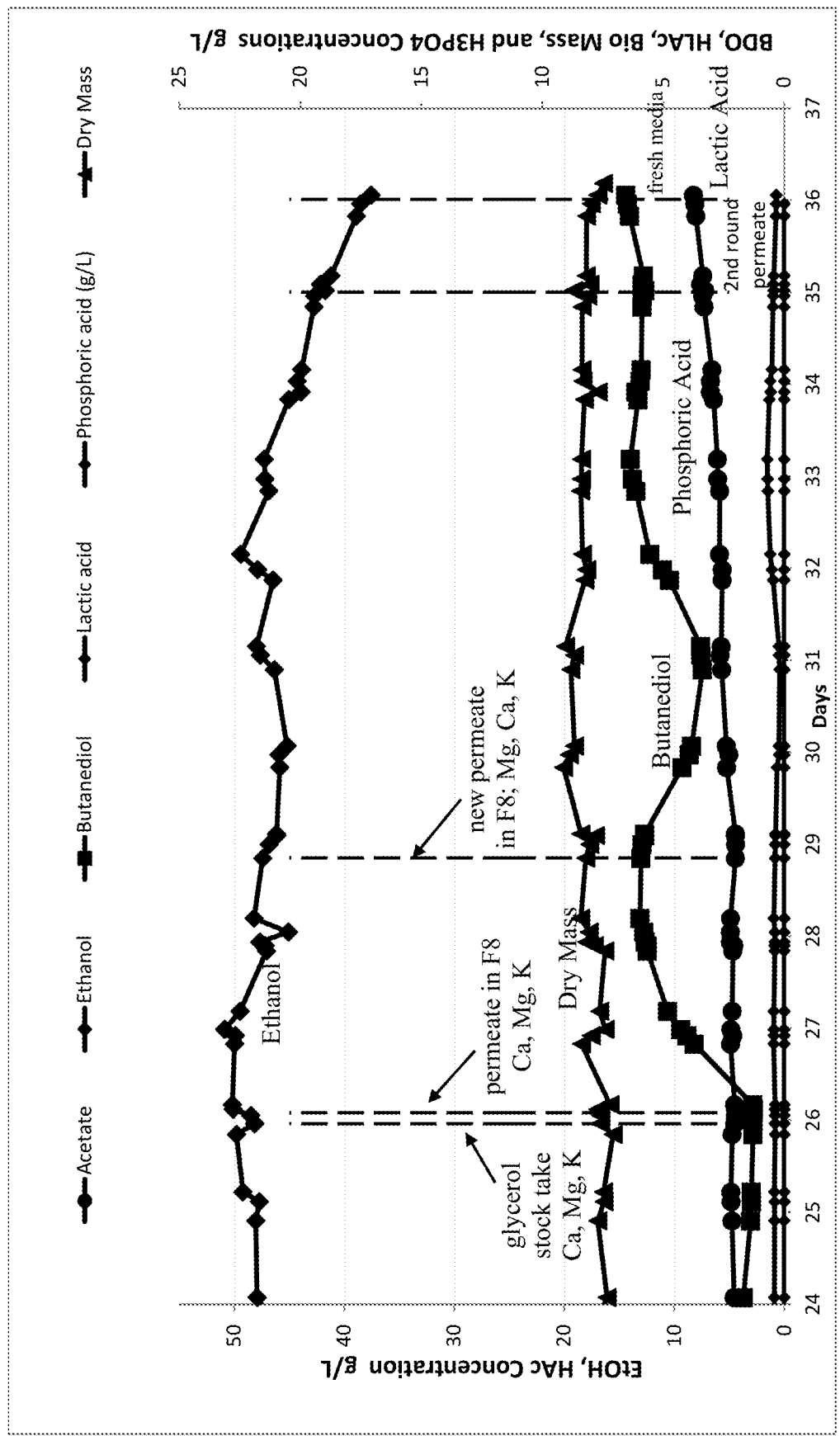
FIG. 8 is a graph showing the metabolite concentration in the second fermenter in the two fermenter system referred to in FIG. 3.
Figure 9:
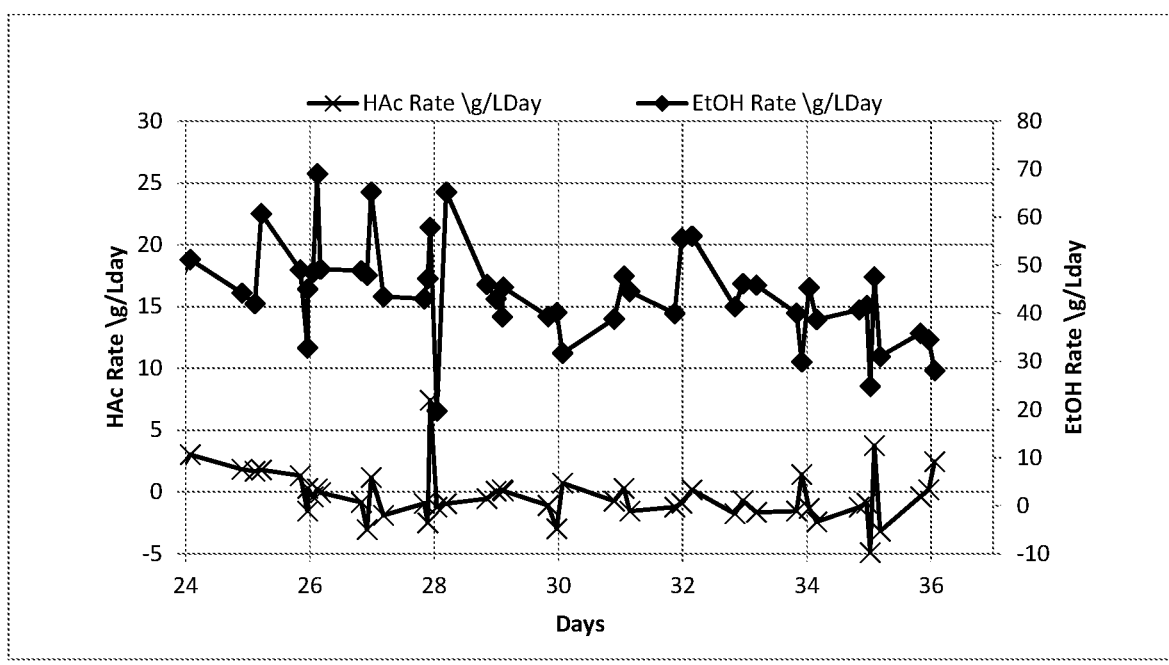
FIG. 9 is a graph showing acetic acid and ethanol production in the second fermenter referred to in FIG. 3.
Figure 10:
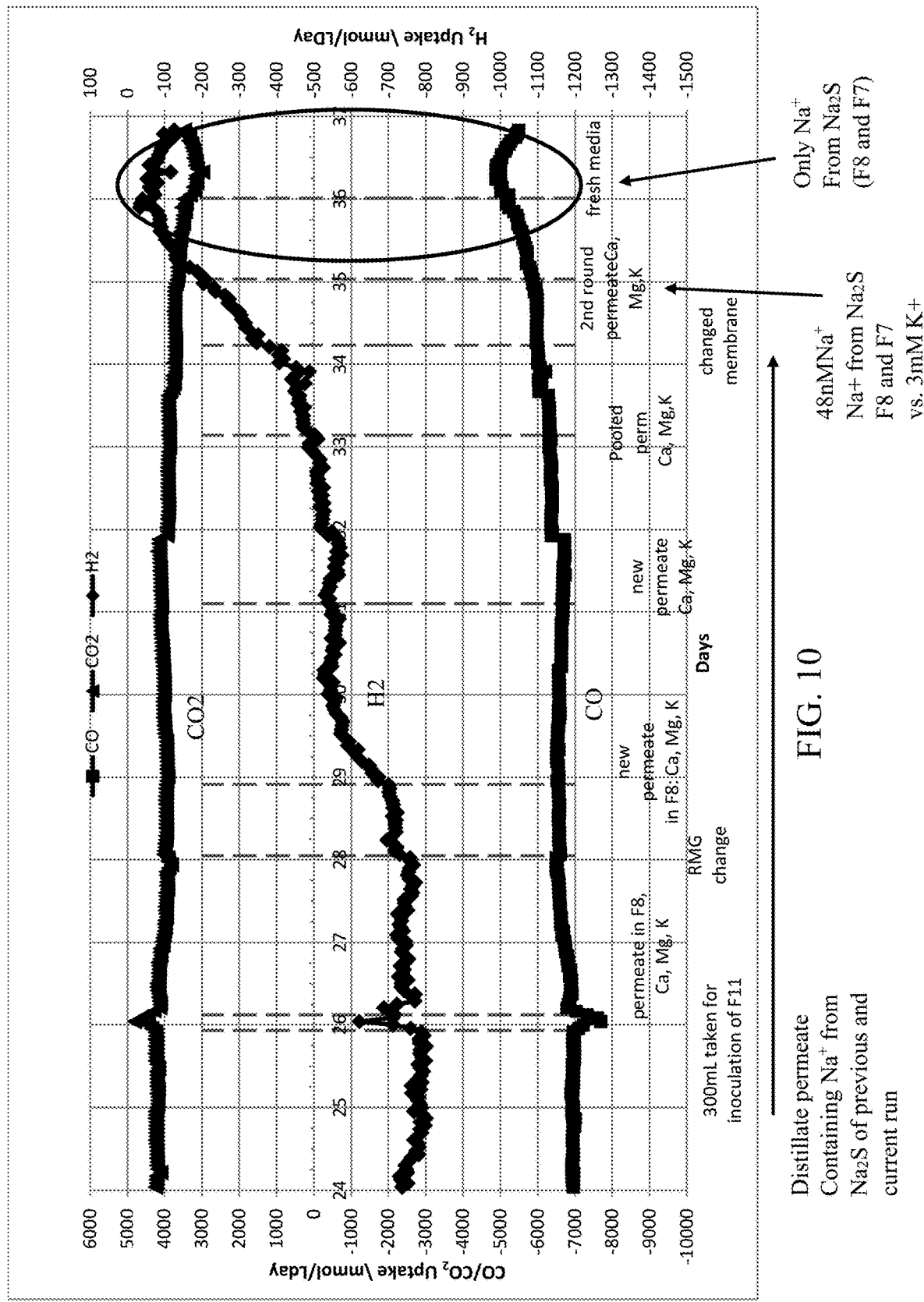
FIG. 10 is a graph showing gas uptake levels in the second fermenter referred to in FIG. 3.
Figure 11:
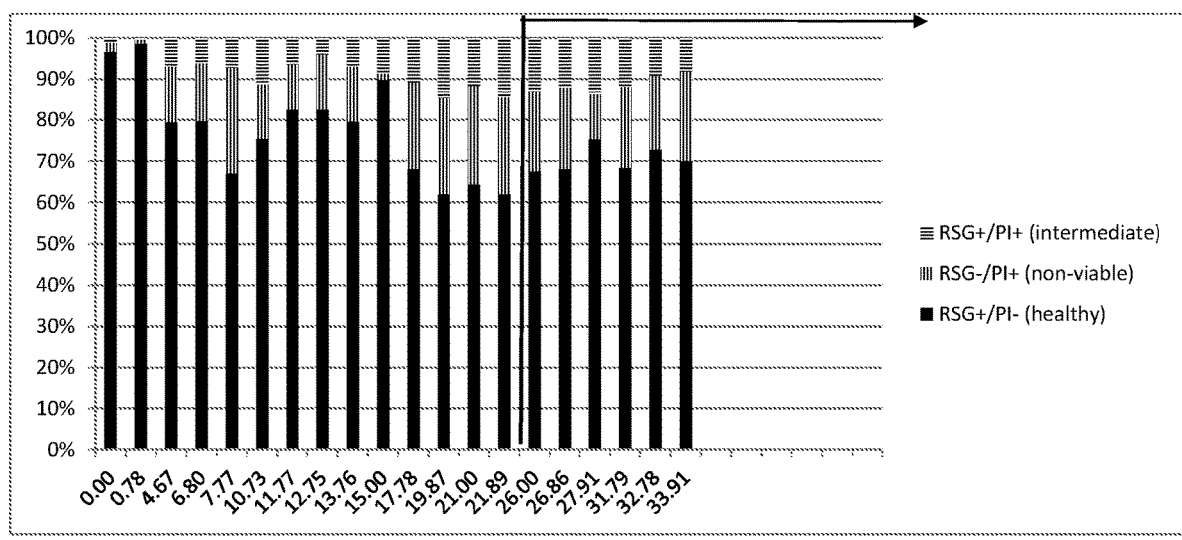
FIG. 11 is a graph showing the cell viability in the second fermenter referred to in FIG. 3.

Metabolite concentrations in fermenters 1 and 2 are shown in FIG. 4 and FIG. 8 respectively. Acetic acid and ethanol production rates are shown in FIG. 5 and FIG. 9 respectively. Gas uptakes in fermenters 1 and 2 are shown in FIG. 6 and FIG. 10 respectively. FIG. 7 and FIG. 11 respectively show the cell viability in the first and second fermenters.

Example 2

Recycling of Waste and Permeate in a 2 Reactor System (100% Recycling)

In this experiment permeate and waste (at a ratio of 1/1) from reactor 2 of a 2 reactor system was collected for a 100% media recycling experiment. The waste was heated to 75° C. and then settled over night to remove the biomass/proteins. After that the settled waste and permeate were distilled to remove Ethanol. In this experiment $Na_2S$ as sulphur source was replaced by dripping $Na_2S$ into concentrated $H_3PO_4$ and the resulting $H_2S$ being carried with the gas inflow into the fermenter. This reduces the Sodium load in the waste and eliminates an excess of sodium as a possible problem when returning the processed waste back into the fermenter.

Figure 12:
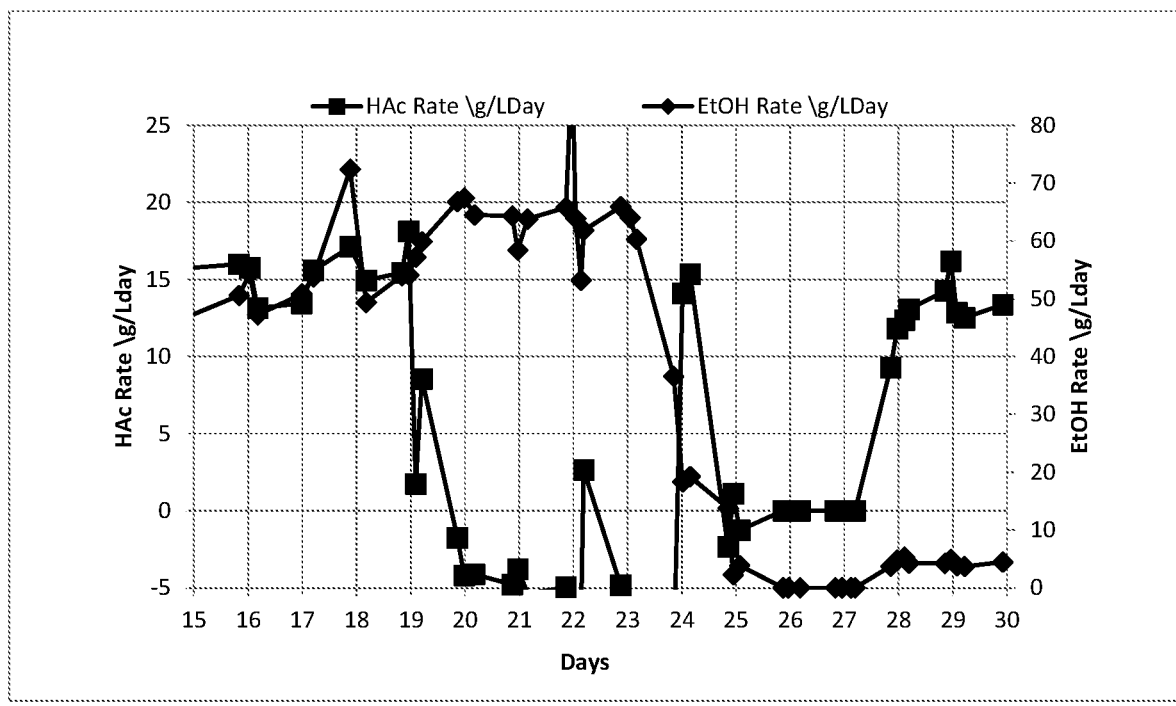
FIG. 12 is a graph showing acetic acid and ethanol production rates in the first fermenter of a two fermenter system during 100% recycling.
Figure 13:
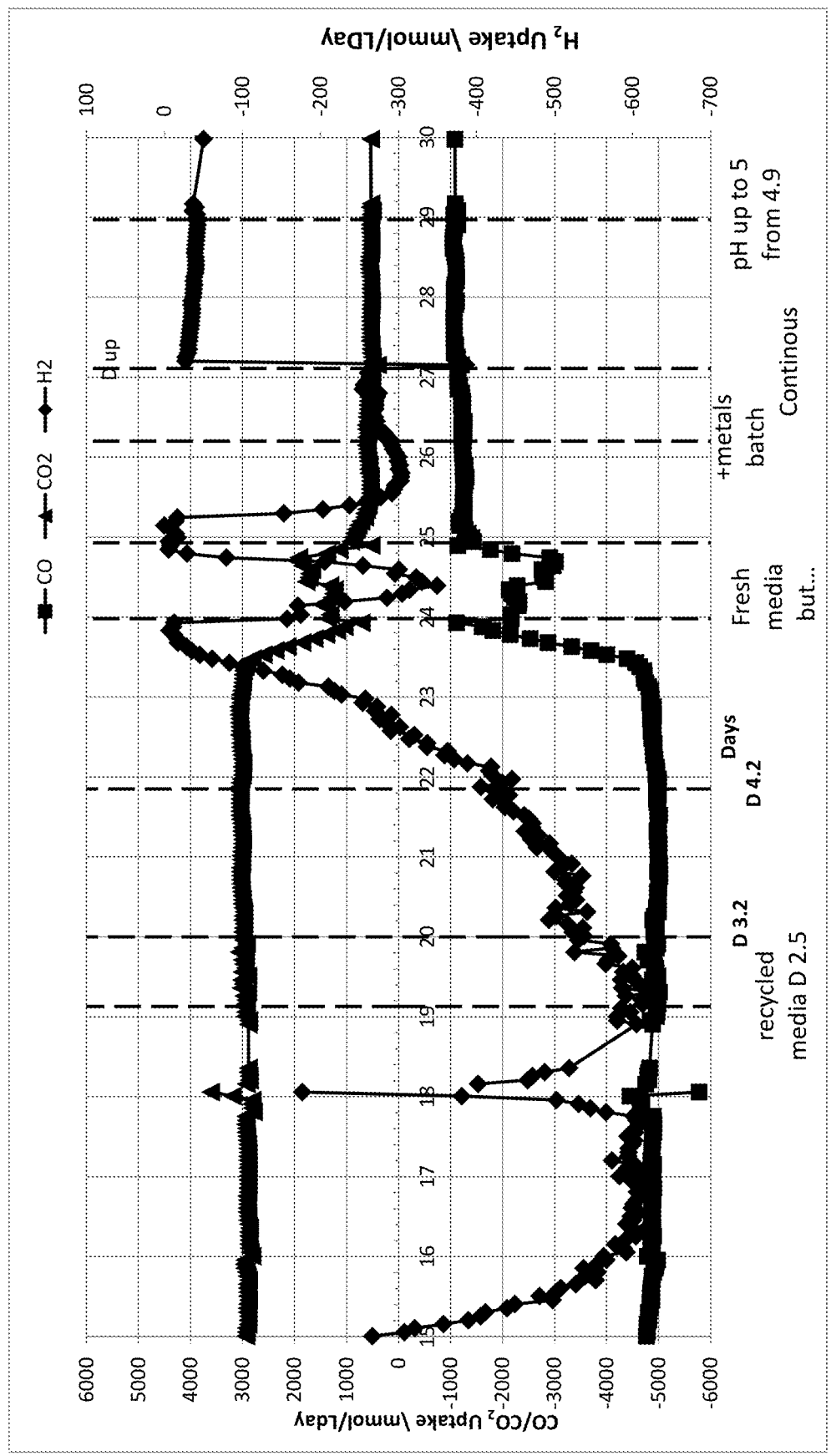
FIG. 13 is a graph showing gas uptake in the first fermenter referred to in FIG. 11.

As shown in FIG. 12, the Ethanol production rate in fermenter 1 increases initially after feeding the recycled media, then stabilizes. Acetic acid production is immediately reduced, then stable at negative rate (media contained 7 g/L acetic acid—concentration falls below 5 g/L while feeding 7 g/L acetic acid).

Figure 14:
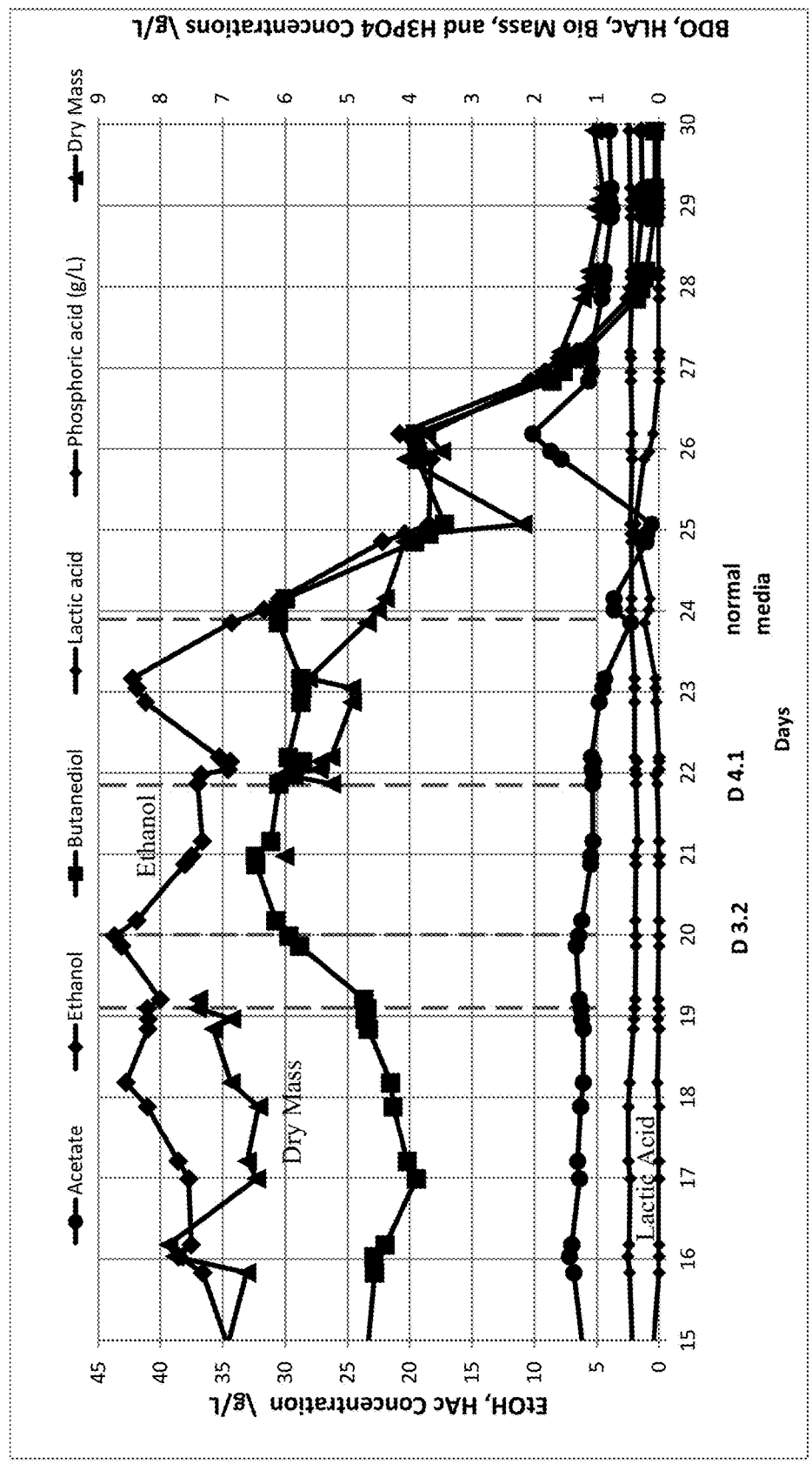
FIG. 14 is a graph showing metabolite levels in the second fermenter of the two fermenter system referred to in FIG. 11.

Biomass is lost during the experiment, probably due to the increase of the dilution rate. The biomass drops from an initial density of 7.5 g/L to 5.2 g/L after 3 days of feeding recycled permeate (FIG. 14). The dilution rate was increased during these 3 days. The rate of the permeate pump may not have been adjusted accordingly. This probably explains the decrease of the gas uptake as shown in FIG. 12. First hydrogen uptake decreases slowly and once this passes a critical value the CO uptake starts to decline rapidly as well. At this point the experiment was stopped and normal media was fed again.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, heading, or the like are provided to enhance the reader's comprehension of this document, and should not be read as limiting the scope of the present invention. The entire disclosures of all applications, patents and publications cited above and below, if any, are herein incorporated by reference.

The reference to any prior art in this specification is not, and should not be taken as, an acknowledgement or any form of suggestion that that prior art forms part of the common general knowledge in the field of endeavour in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What is claimed is:

1. A method for improving carbon capture in a microbial fermentation of a substrate comprising CO, the method comprising;
   a) in a bioreactor comprising a culture of at least one microorganism, fermenting a gaseous substrate comprising CO to produce a fermentation broth comprising at least one product;
   b) removing at least a portion of the fermentation broth via a bleed stream, from the bioreactor;
   c) removing at least a portion of a permeate stream from the bioreactor;
   d) removing at least a portion of the at least one product from the bleed stream and/or permeate stream to provide a product depleted stream;
   e) passing the product depleted stream to a clarifying module wherein at least a portion of biomass contained in the product depleted stream is removed from the product depleted stream to provide a treated stream; and
   f) passing at least a portion of the treated stream to the bioreactor.

2. The method of claim 1 wherein the at least one product is an alcohol or an acid.

3. The method of claim 1 wherein the at least one product is selected from the group consisting of ethanol, acetic acid and 2,3-butanediol.

4. The method of claim 1 wherein at least a portion of the at least one product removed in step (d) is removed by a distillation process.

5. The method of claim 1 wherein the clarifying module comprises an anaerobic digestion module.

6. The method of claim 1 wherein the clarifying module comprises at least one of a biomass removal module, an organic component removal module, an inorganic component removal module, an acid removal module or a sterilisation module.

7. The method of claim 5 wherein the anaerobic digestion module consumes biomass and/or proteins and produces a gaseous substrate comprising methane and carbon dioxide.

8. The method of claim 7 wherein the methane produced by the anaerobic digestion is used as a carbon, heat or energy source.

9. The method of claim 7 wherein the methane is used in a process selected from the group consisting of; reformation of methane to produce to CO; direct or indirect heating of a distillation process for the removal of at least one product from a permeate and/or bleed stream; and power generation using a gas turbine.

10. The method of claim 1 further comprising adding at least one component of a liquid nutrient media to the treated stream prior to the treated stream being passed back to the bioreactor.

11. The method of claim 1 wherein the microbial fermentation is a continuous microbial fermentation.

12. The method of claim 1 wherein the steps (d) and (e) are carried out continuously.

13. The method of claim 1, wherein the microorganism is *A. woodii*; the gaseous substrate is $CO_2$ and $H_2$; and the at least one product is acetic acid.

14. The process of claim 1 where the at least one microorganism is a carboxydotrophic acetogenic bacteria.

15. The process of claim 1 where the at least one microorganism is selected from the genus *Clostridium*.

16. The process of claim 15 where the at least one microorganism is selected from the group consisting of *Clostridium autoethanogenum, Clostridium ljungdahlii, Clostridium ragsdalei, Clostridium carboxidivorans* and *Clostridium coskatii*.

17. The process of claim 16 where the at least one microorganism is *Clostridium autoethanogenum*.

18. The method of claim 10 wherein the one or more components of the liquid nutrient media is selected from the group consisting of Iron, Potassium, Calcium, Magnesium, Boron, Cobalt, Chromium, Manganese, Molybdenum, Sodium, Nickel, Selenium, Zinc, Chloride, Phosphorus, Sulphide, Nitrogen, Tungsten and B vitamins.

\* \* \* \* \*